United States Patent
Liu et al.

(10) Patent No.: US 12,162,876 B2
(45) Date of Patent: Dec. 10, 2024

(54) INDAZOLE KINASE INHIBITOR AND USE THEREOF

(71) Applicant: Tarapeutics Science Inc., Bengbu (CN)

(72) Inventors: Jing Liu, Anhui (CN); Qingsong Liu, Anhui (CN); Xuesong Liu, Anhui (CN); Beilei Wang, Anhui (CN); Cheng Chen, Anhui (CN); Ziping Qi, Anhui (CN); Wenchao Wang, Anhui (CN); Junjie Wang, Anhui (CN); Zongru Jiang, Anhui (CN); Wenliang Wang, Anhui (CN); Shuang Qi, Anhui (CN); Li Wang, Anhui (CN)

(73) Assignee: Tarapeutics Science Inc., Bengbu (CN)

(*) Notice: Subject to any disclaimer, the term of this patent is extended or adjusted under 35 U.S.C. 154(b) by 764 days.

(21) Appl. No.: 17/288,966

(22) PCT Filed: Nov. 12, 2018

(86) PCT No.: PCT/CN2018/115025
§ 371 (c)(1),
(2) Date: Apr. 27, 2021

(87) PCT Pub. No.: WO2020/087565
PCT Pub. Date: May 7, 2020

(65) Prior Publication Data
US 2022/0002287 A1    Jan. 6, 2022

(30) Foreign Application Priority Data

Nov. 2, 2018 (CN) .................. 201811299323.X

(51) Int. Cl.
| | | |
|---|---|---|
| *C07D 417/14* | (2006.01) | |
| *A61P 1/00* | (2006.01) | |
| *A61P 35/00* | (2006.01) | |
| *C07D 417/04* | (2006.01) | |

(52) U.S. Cl.
CPC .............. *C07D 417/14* (2013.01); *A61P 1/00* (2018.01); *A61P 35/00* (2018.01); *C07D 417/04* (2013.01)

(58) Field of Classification Search
CPC ..... C07D 417/14; C07D 231/56; A61P 35/00; A61P 1/00; A61K 31/38; A61K 31/416; A61K 31/426; A61K 31/4365
See application file for complete search history.

(56) References Cited

U.S. PATENT DOCUMENTS

2008/0182844 A1    7/2008 Bjergarde et al.

FOREIGN PATENT DOCUMENTS

| CN | 101790526 A | 7/2010 | |
| CN | 102958927 A | 3/2013 | |
| CN | 103080093 A | 5/2013 | |
| CN | 102134234 B | 6/2013 | |
| WO | 2008/005877 A2 | 1/2008 | |
| WO | 2010/064875 A2 | 6/2010 | |
| WO | WO-2011143430 A1 * | 11/2011 | ........... C07D 401/14 |
| WO | 2017027400 A1 | 2/2017 | |
| WO | 2019/119481 A1 | 6/2019 | |

OTHER PUBLICATIONS

Silverman. Organic Chemistry of Drug Design and Drug Action, Elservier Academic Press, 2004, p. 24-34 (Year: 2004).*
Caenepeel. Journal of Experimental & Clinical Cancer Research 2010, 29:96, p. 1-8 (Year: 2010).*
Rutkowski (A. Russo et al. (eds.), Targeted Therapies for Solid Tumors, Current Clinical Pathology—Chapter 14, © Springer Science+Business Media New York 2015 (Year: 2015).*
Liu et al. Axitinib overcomes multiple . . . , Ther Adv Med Oncol. 2019, vol. 11: 1-15 (Year: 2019).*
International Search Report dated Feb. 25, 2019 issued in PCT/CN2018/115025.
Vojtickova M. et al., "Ynamide Click Chemistry in Development of Triazole VEGFR2 TK Modulators", European Journal of Medicinal Chemistry 103:105-122 (Aug. 8, 2015).
Von Mehren M., "Beyond Imatinib: Second Generation c-KIT Inhibitors for the Management of Gastrointestinal Stromal Tumors", Clinical Colorectal Cancer 6(1):S30-S34 (Jan. 1, 2006).
Extended European Search Report dated Jul. 6, 2022 received in European Application No. 18 938 587.5.

* cited by examiner

*Primary Examiner* — Kortney L. Klinkel
*Assistant Examiner* — Richard Grant Peckham
(74) *Attorney, Agent, or Firm* — Scully, Scott, Murphy & Presser, P.C.

(57) ABSTRACT

Described herein is a kinase inhibitor compound represented by formula (I) or a pharmaceutically acceptable salt, solvate, ester, acid, metabolite or prodrug of the compound. Further described herein is a pharmaceutical composition containing the kinase inhibitor compound, as well as methods of using the compound to inhibit cKIT (especially mutant cKIT/T670I), FLT3 (comprising mutant FLT3-ITD), PDGFRα, PDGFRβ, and/or VEGFR2 kinase activity in cells or a subject, and methods for preventing or treating disorders related to cKIT (especially mutant cKIT/T670I), FLT3 (comprising mutant FLT3-ITD), PDGFRα, PDGFRβ, and/or VEGFR2 activity in a subject.

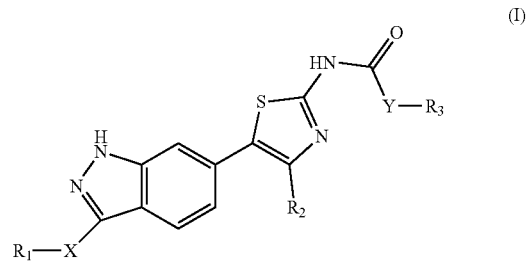

13 Claims, 2 Drawing Sheets

INDAZOLE KINASE INHIBITOR AND USE THEREOF

FIELD OF THE INVENTION

The present application relates to a kinase inhibitor, as well as a method and use for inhibiting kinase activity using such kinase inhibitor. More specifically, the present invention relates to an inhibitor capable of inhibiting the kinase activity of cKIT (especially mutant cKIT/T670I), FLT3 (including mutant FLT3-ITD), PDGFRα, PDGFRβ, and/or VEGFR2.

BACKGROUND OF THE INVENTION

Gastrointestinal stromal tumors (GIST) are the most common mesenchymal tumors of the gastrointestinal tract. The incidence of GIST is about 1/100,000 to 2/100,000, accounting for 1-3% of all gastrointestinal tumors. The disease is more common in middle-aged and elderly people, the median age of onset is 50 to 65 years old, it is rare before 40 years old, but it has also been reported in children. At present, GIST is considered to be a tumor with potentially malignant behavior, and its biological behavior is difficult to predict. GIST can occur in any part of the digestive tract, the most common in the stomach (60%~70%), followed by the small intestine (20%~30%), the incidence of less than 10% in the esophagus, colon, and rectum, and can also occur in the omentum and mesenterium.

According to clinical studies, the pathogenesis of gastrointestinal stromal tumors can be divided into three categories based on their genetic molecular classification: cKIT mutant (80-85%), PDGFRα mutant (5-10%) and cKIT wild-type GISTs (10%). The pathogenesis of gastrointestinal stromal tumors is related to the activation of cKIT protein (CD117) signaling pathway. The proto-oncogene cKIT, a homologue of the vKIT gene isolated from the feline fibrosarcoma virus, is located on the human chromosome 4 (4q12-13) and is about 90 kb in length; it consists of 21 exons and 20 introns, and it is highly conserved during evolution. The cKIT protein is a receptor tyrosine kinase (RTK) located on the cell membrane, with a relative molecular weight of 145,000, and is named as CD117 according to its antigenic determinants on the surfaces of cells. The cKIT protein belongs to the third type of RTK family; it consists of 5 immunoglobulin-like domains (D1~D5), 1 transmembrane domain, and 1 cytoplasmic region containing near membrane domain (JMD) and tyrosine kinase (TK) domain. The TK domain is divided into adenosine triphosphate (ATP) domain (TK1) and phosphotransferase domain (TK2). The ligand stem cell factor (SCF) combines with the extracellular domain to form a dimer, leading to autophosphorylation of tyrosine in the TK domain of the cytoplasmic region, which further induces autophosphorylation of various downstream effectors and completes the delivery of various signals. The main signaling pathways include PI3K signaling pathway, JAK-STAT signaling pathway, Ras-Erk signaling pathway, Src family kinase signaling pathway, and PLC signaling pathway, etc., which ultimately promote cell proliferation, division, and tissue growth and survival.

At present, as a traditional surgical treatment method, surgery is still the most important method for the treatment of gastrointestinal stromal tumors, and the emergence of targeted drugs in recent years has opened a new stage in the treatment of GIST. So far, the clinically used cKIT kinase inhibitors for the treatment of GIST mainly include Imatinib (cKIT/BCR-ABL/PDGFR) from Novartis and Sunitinib (cKIT/BCR-ABL/PDGFR/VEGFR2/FLT3) from Pfizer. Imatinib is the first type II kinase inhibitor used for the treatment of GIST. Sunitinib is a type I cKIT kinase inhibitor approved by the FDA in 2006. In addition, type II kinase inhibitors with cKIT activity include Regorafenib, Nilotinib, Mastinib, Sorafenib, etc. These small molecule inhibitors are multi-target inhibitors, and Nilotinib and Mastinib cannot overcome the T670I mutation. Although two small molecule inhibitors with cKIT activity, Regorafenib and Sorafenib developed by Bayer, have certain activity against the cKIT-T670I mutation, they are both multi-target inhibitors, in addition to cKIT, they also have a strong effect on a variety of kinases such as FLT3/PDGFR/FGFR/VEGFR2/RET/RAF. Axitinib is a multi-target small molecule inhibitor developed by Pfizer, and it also has the inhibitory activity on cKIT, BCR-ABL, VEGFR2 and other kinases. In addition, Ponatinib also has a strong inhibitory activity on cKIT kinase, and at the same time, it can overcome the drug-resistance caused by the cKIT-T670I mutation, but it is a multi-target inhibitor of various kinases such as ABL/PDGFR/RET/CSF1R/FGFR/VEGFR/FGFR/RET.

The present invention mainly discovers an inhibitor with a novel structure that has a strong inhibitory effect on Imatinib drug-resistant mutation cKIT-T670I.

SUMMARY OF THE INVENTION

The present invention provides a selective kinase inhibitor, comprising a compound of formula (I), or a pharmaceutically acceptable salt, solvate, ester, acid, metabolite or prodrug thereof:

Formula (I)

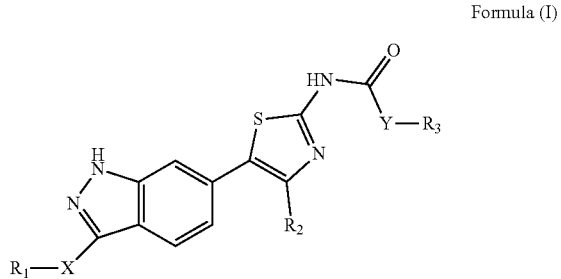

wherein,

X is —(CH═CH)$_m$—, where m is 0 or 1;

Y is selected from a group consisting of —NH— or —(CH$_2$)$_n$—, where n is an integer of 0 to 3;

R$_1$ is selected from a group consisting of phenyl optionally substituted with 1-3 independent R$_4$ groups, pyridinyl optionally substituted with 1-3 independent R$_4$ groups, pyrazolyl optionally substituted with 1-3 independent R$_4$ groups, and pyrimidinyl optionally substituted with 1-3 independent R$_4$ groups;

R$_2$ is selected from a group consisting of hydrogen and C$_{1-6}$ alkyl;

R$_3$ is selected from a group consisting of C$_{1-6}$ alkyl optionally substituted with 1-2 independent R$_5$ groups, C$_{1-6}$ alkylamino, as well as phenyl optionally substituted with 1-3 independent R$_4$ groups, naphthyl optionally substituted with 1-3 independent R$_4$ groups, pyridinyl optionally substituted with 1-3 independent R$_4$ groups, piperazinyl optionally substituted with 1-3 independent R$_4$ groups, and piperidyl optionally substituted with 1-3 independent R$_4$ groups;

$R_4$ is independently selected from a group consisting of halogen, amino, $C_{1-6}$ alkyl, $C_{3-6}$ cycloalkyl, $C_{1-6}$ haloalkyl, $C_{1-6}$ alkoxy, $C_{1-6}$ hydroxyalkyl, $C_{1-6}$ alkylamino, $C_{2-6}$ alkylamide, (4-methylpiperazin-1-yl) methyl, morpholinomethyl, morpholinyl, 4-methylpiperazin-1-yl, 4-piperidyl, and 4-tetrahydropyranyl;

$R_5$ is independently selected from a group consisting of amino, hydroxyl, and $C_{1-6}$ alkylthio.

In a preferred embodiment, X is —(CH=CH)—.

In another preferred embodiment, Y is a direct bond or —CH$_2$—.

In another preferred embodiment, $R_1$ is selected from a group consisting of phenyl, pyridinyl, pyrazolyl, and pyrimidinyl groups optionally substituted with 1-3 independent $R_4$ groups, wherein $R_4$ is independently selected from a group consisting of halogen, amino, $C_{1-6}$ alkyl, $C_{1-6}$ haloalkyl, $C_{1-6}$ alkoxy, and (4-methylpiperazin-1-yl)methyl; $R_1$ is more preferably phenyl, 2-pyridinyl, 3-pyridinyl, 4-pyrazolyl, and 5-pyrimidinyl groups optionally substituted with methyl, amino or halogen; $R_1$ is particularly preferably 2-pyridinyl.

In another preferred embodiment, $R_2$ is hydrogen or methyl.

In another preferred embodiment, $R_3$ is selected from a group consisting of $C_{1-6}$ alkyl optionally substituted with 1-2 independent $R_5$ groups, $C_{1-6}$ alkylamino, as well as phenyl, naphthyl, pyridinyl, piperazinyl, and piperidyl groups optionally substituted with 1-3 independent $R_4$ groups, wherein $R_4$ is independently selected from a group consisting of halogen, amino, $C_{1-6}$ alkyl, $C_{1-6}$ haloalkyl, $C_{1-6}$ alkoxy, and (4-methylpiperazin-1-yl)methyl, $R_5$ is independently selected from a group consisting of amino, hydroxyl, and methylthio; $R_3$ is more preferably $C_{1-6}$ alkyl optionally substituted with amino, hydroxy or methylthio; dimethylamino; N-piperazinyl optionally substituted with methyl; phenyl, optionally substituted with halogen, trifluoromethyl or methoxy; naphthyl; 4-pyridinyl; 3-piperidyl; and 4-piperidyl optionally substituted with methyl; $R_3$ is particularly preferably methyl, 2-propyl, 1-amino-3-methylthio-propyl, 1-amino-3-methyl-butyl, methyl-substituted N-piperazinyl, methoxy-substituted phenyl, 4-pyridinyl, or 4-piperidyl.

In a particularly preferred embodiment, when Y is a direct bond, $R_3$ is selected from a group consisting of $C_{1-6}$ alkyl optionally substituted with amino, hydroxy or methylthio, and 4-pyridinyl; and when Y is —CH$_2$—, $R_3$ is selected from a group consisting of phenyl optionally substituted with methoxy, N-piperazinyl optionally substituted with methyl, and 4-piperidyl optionally substituted with methyl.

In another aspect, the present invention also relates to a pharmaceutical composition, comprising the kinase inhibitor of the present invention, and a pharmaceutically acceptable carrier or excipient, as well as optionally other therapeutic agents.

In other aspects, the present invention also relates to a method and use of the kinase inhibitor or the pharmaceutical composition comprising the same for reducing or inhibiting the kinase activity of cKIT (especially mutant cKIT/T670I), FLT3 (including mutant FLT3-ITD), PDGFRα, PDGFRβ, and/or VEGFR2 in cells or subjects.

In yet another aspect, the present invention also relates to a method and use of the kinase inhibitor or the pharmaceutical composition comprising the same for preventing or treating a disease related to the activity of cKIT (especially mutant cKIT/T670I), FLT3 (including mutant FLT3-ITD), PDGFRα, PDGFRβ, and/or VEGFR2 in a subject.

DETAILED DESCRIPTION OF THE INVENTION

Terminology

Figure 1A:
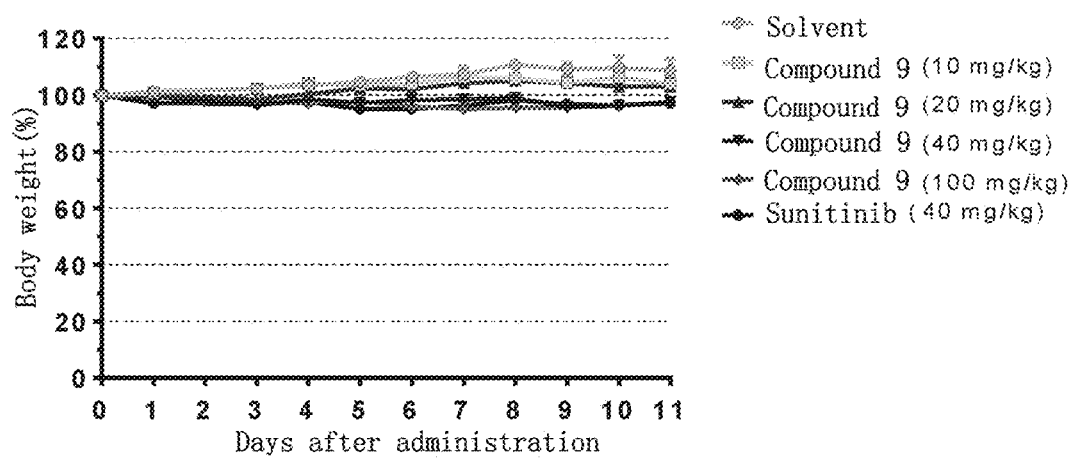
FIG. 1a shows the effects of Compound 9 and Sunitinib on the body weight of mice after administration in the tel-cKIT/T670I-BaF3 cell tumor transplantation mouse models.

Unless defined otherwise, all technical and scientific terms used herein have the same meaning as is commonly understood by one of skill in the art to which the claimed subject matter belongs.

Unless otherwise indicated, conventional methods of mass spectroscopy, NMR, HPLC, protein chemistry, biochemistry, recombinant DNA techniques and pharmacology, within the skill of the art are employed in the invention. Unless specific definitions are provided, the nomenclature employed in connection with, and the laboratory procedures and techniques of, analytical chemistry, synthetic organic chemistry, and medicinal and pharmaceutical chemistry described herein are those known in the art. The foregoing techniques and procedures can be generally performed of conventional methods well known in the art and as described in various general and more specific references that are cited and discussed throughout the present specification.

The term "alkyl" refers to an aliphatic hydrocarbon group, which may be branched or straight alkyl. Depending on the structure, an alkyl group may be a monoradical or a diradical (i.e., an alkylene group). In the invention, the alkyl group is preferably an alkyl having 1 to 8 carbon atoms, more preferably a "lower alkyl" having 1 to 6 carbon atoms, and even more preferably an alkyl having 1 to 4 carbon atoms. Typical alkyl groups include, but are not limited to, methyl, ethyl, propyl, butyl, pentyl, hexyl, and the like. It should be understood that the "alkyl" as mentioned herein encompasses all configurations and conformations that may exist of the alkyl, e.g., the "propyl" as mentioned herein intends to encompass n-propyl and isopropyl, "butyl" as mentioned herein intends to encompass n-butyl, isobutyl, and tertiary butyl, and "pentyl" as mentioned herein intends to encompass n-pentyl, isopentyl, neopentyl, tert-pentyl, pent-3-yl, etc.

The term "alkoxy" refers to a —O-alkyl group, where alkyl is as defined herein. Typical alkoxy groups include, but are not limited to, methoxy, ethoxy, propoxy, butoxy, pentyloxy, hexyloxy, and the like.

The term "alkoxy alkyl" refers to an alkyl group as defined herein that is substituted with alkoxy as defined herein.

The term "cycloalkyl" refers to a monocyclic or polycyclic radical that contains only carbon and hydrogen. Cycloalkyl groups include groups having from 3 to 12 ring atoms. Depending on the structure, a cycloalkyl group can be a monoradical or a diradical (e.g., a cycloalkylene group). In the invention, the cycloalkyl group is preferably a cycloalkyl having 3 to 8 carbon atoms, and more preferably a "lower cycloalkyl" having 3 to 6 carbon atoms. Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl.

The term "alkyl(cycloalkyl)" or "cycloalkylalkyl" refers to an alkyl group as defined herein that is substituted with cycloalkyl as defined herein. Non-limiting examples of cycloalkylalkyl include cyclopropylmethyl, cyclobutylmethyl, cyclopentylmethyl, cyclohexylmethyl, etc.

The term "aromatic" refers to a planar ring having a delocalized π-electron system containing 4n+2π electrons, where n is an integer. Aromatic rings can be formed by five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

The term "aryloxy" refers to —O-aryl, wherein aryl is as defined herein.

The term "heteroaryl" refers to an aryl group that includes one or more ring heteroatoms selected from nitrogen, oxygen and sulfur. An N-containing "heteroaryl" moiety refers to an aromatic group in which at least one of the skeletal atoms of the ring is a nitrogen atom. Depending on the structure, the heteroaryl group may be a monoradical or a diradical (i.e., a heteroarylene group). Examples of heteroaryl groups include, but are not limited to pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuryl, indazolyl, indolizinyl, phthalazinyl, pyridazinyl, isoindolyl, pteridinyl, purinyl, oxadiazolyl, thiadiazolyl, furyl, benzofuryl, benzothiophenyl, benzothiazolyl, benzoxazolyl, quinazolinyl, naphthyridinyl, furopyridinyl, and the like.

The term "alkyl(aryl)" or "aralkyl" refers to an alkyl group as defined herein substituted with aryl as defined herein. Non-limiting alkyl(aryl) groups include benzyl, phenethyl, and the like.

The term "alkyl(heteroaryl)" or "heteroarylalkyl" refers to an alkyl group as defined herein that is substituted with heteroaryl as defined herein.

As used herein, the term "heteroalkyl" refers to an alkyl group, as defined herein, in which one or more skeletal chain atoms is a heteroatom, e.g., oxygen, nitrogen, sulfur, silicon, phosphorus or combinations thereof. The heteroatom(s) may be placed at any interior position of the heteroalkyl group or at the position at which the heteroalkyl group is attached to the remainder of the molecule.

As used herein, the term "heterocycloalkyl" or "heterocyclyl" refers to a non-aromatic ring wherein one or more atoms forming the ring is a heteroatom selected from nitrogen, oxygen and sulfur. Heterocycloalkyl rings can be formed by three, four, five, six, seven, eight, nine, or more than nine atoms. Heterocycloalkyl rings can be optionally substituted. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, imidazolidine, pyrrolidone, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Depending on the structure, a heterocycloalkyl group can be a monoradical or a diradical (i.e., a heterocycloalkylene group).

The term "alkyl(heterocycloalkyl)" or "heterocycloalkylalkyl" refers to an alkyl group as defined herein that is substituted with heterocycloalkyl as defined herein.

The term "alkoxy(heterocycloalkyl)" or "heterocycloalkylalkoxy" refers to an alkoxy group as defined herein that is substituted with heterocycloalkyl as defined herein.

The term "halo" or "halogen" refers to fluoro, chloro, bromo and iodo.

The terms "haloalkyl", "haloalkoxy" and "haloheteroalkyl" include alkyl, alkoxy and heteroalkyl structures in which at least one hydrogen is replaced with a halogen atom. In certain embodiments in which two or more hydrogen atoms are replaced with halogen atoms, the halogen atoms are the same or different as one another.

The term "hydroxy" refers to —OH group.

As used herein, the term "cyano" refers to —CN group.

The term "ester" refers to a chemical moiety with formula —COOR, where R is selected from among alkyl, cycloalkyl, aryl, heteroaryl (bonded through a ring carbon) and heterocyclic (bonded through a ring carbon).

The term "amino" refers to —NH$_2$ group.

The term "aminoacyl" refers to —CO—NH$_2$ group.

The term "amide" or "amido" refers to —NR—CO—R', wherein each of R and R' is independently hydrogen or alkyl.

The term "alkylamino" refers to an amino substituent which is further substituted with one or two alkyl groups, specifically the group —NRR', wherein R and R' are each independently selected from a group consisting of hydrogen or lower alkyl, with the proviso that —NRR' is not —NH$_2$. "Alkylamino" includes groups of compounds in which nitrogen of —NH$_2$ is bound to at least one alkyl group. Examples of alkylamino groups include, but are not limited to, methylamino, ethylamino, and the like. "Dialkylamino" includes groups in which the nitrogen of —NH$_2$ is bound to at least two additional alkyl groups. Examples of dialkylamino groups include, but are not limited to, dimethylamino, diethylamino, and the like.

The terms "arylamino" and "diarylamino" refer to amino substituents further substituted with one or two aryl groups, and specifically refer to the group —NRR', wherein R and R' are each independently selected from hydrogen, lower alkyl or aryl, wherein N is connected to at least one or two aryl groups, respectively.

The term "cycloalkylamino" refers to an amino substituent further substituted with one or two cycloalkyl groups as defined herein.

The term "heteroalkylamino" refers to an amino substituent further substituted with one or two heteroalkyl groups as defined herein.

The term "aralkylamino" herein refers to a group —NRR' in which R is a lower aralkyl and R' is hydrogen, lower alkyl, aryl, or lower aralkyl.

The term "heteroarylamino" refers to an amino substituent further substituted with one or two heteroaryl groups as defined herein.

The term "heterocycloalkylamino" refers to an amino group as defined herein that is substituted with heterocycloalkyl as defined herein.

The term "alkylaminoalkyl" refers to an alkyl group as defined herein that is substituted with alkylamino as defined herein.

The term "aminoalkyl" refers to an alkyl substituent further substituted with one or more amino groups.

The term "aminoalkoxy" refers to an alkoxy substituent further substituted with one or more amino groups.

The term "hydroxyalkyl" or "hydroxyl alkyl" refers to an alkyl substituent further substituted with one or more hydroxy groups.

The term "cyanoalkyl" refers to an alkyl substituent further substituted with one or more cyano groups.

The term "acyl" refers to the monovalent atomic group remaining after removing the hydroxyl group from an organic or inorganic oxyacid, and the general formula is R-M(O)—, wherein M is usually C.

The term "carbonyl" is an organic functional group (C=O) formed by carbon atom and oxygen atom through a double bond linkage.

The term "alkanoyl" or "alkylcarbonyl" refers to a carbonyl group further substituted with an alkyl group. Typical alkanoyl groups include, but are not limited to, acetyl, propionyl, butyryl, valeryl, hexanoyl and the like.

The term "arylcarbonyl" refers to a carbonyl group as defined herein that is substituted with aryl as defined herein.

The term "alkoxycarbonyl" refers to a carbonyl group further substituted with an alkoxy group.

The term "heterocycloalkylcarbonyl" refers to a carbonyl group further substituted with a heterocycloalkyl group.

The terms "alkylaminocarbonyl", "cycloalkylaminocarbonyl", "arylaminocarbonyl", "aralkylaminocarbonyl", and "heteroarylaminocarbonyl" respectively refer to carbonyl groups as defined herein that are substituted with alkylamino, cycloalkylamino, arylamino, aralkylamino, or heteroarylamino as defined herein, respectively.

The term "alkylcarbonylalkyl" or "alkanoylalkyl" refers to an alkyl group further substituted with an alkylcarbonyl group.

The term "alkylcarbonylalkoxy" or "alkanoylalkoxy" refers to an alkoxy further substituted with an alkylcarbonyl group.

The term "heterocycloalkylcarbonylalkyl" refers to an alkyl group further substituted with a heterocycloalkylcarbonyl group.

The term "sulfhydryl" refers to —SH group. The term "alkylthio" refers to an sulfhydryl group as defined herein that is substituted with alkyl as defined herein.

The term "sulfone" or "sulfonyl" refers to a functional group of the sulfonic acid after losing hydroxyl, and specifically refers to —S(=O)$_2$— group.

The term "sulfoxide" or "sulfinyl" refers to —S(=O)—.

The term "aminosulfone" or "aminosulfonyl" refers to —S(=O)$_2$—NH$_2$ group.

The term "alkylsulfoxide" or "alkylsulfinyl" refers to —S(=O)—R, wherein R is alkyl.

The term "alkylsulfone" or "alkylsulfonyl" refers to —S(=O)$_2$—R, wherein R is alkyl.

The term "alkylaminosulfone" refers to a sulfone group as defined herein that is substituted with alkylamino as defined herein.

The term "alkylsulfoneamino" or "cycloalkylsulfoneamino" refers to an amino group as defined herein that is substituted with alkylsulfone or cycloalkylsulfone as defined herein.

The terms "cycloalkylsulfone" and "cycloalkylsulfonyl" refer to —S(=O)$_2$—R, wherein R is a cycloalkyl.

The terms "alkylsulfonamido" and "cycloalkylsulfonamido" refer to —NH—S(=O)$_2$—R, wherein R is alkyl and cycloalkyl, respectively.

The term "quaternary ammonium group" refers to —N$^+$RR'R", wherein R, R' and R" are each independently selected from alkyl groups having 1-8 carbon atoms.

The term "optionally" means that the subsequently described event(s) may occur or may not occur, and includes both event(s), which occur, and events that do not occur. The term "optionally substituted" or "substituted" means that the referenced group may be substituted with one or more additional group(s) individually and independently selected from a group consisting of alkyl, cycloalkyl, aryl, heteroaryl, heterocyclyl, hydroxy, alkoxy, cyano, halo, amide, nitro, haloalkyl, amino, methylsulfonyl, alkylcarbonyl, alkoxycarbonyl, heteroarylalkyl, heterocycloalkylalkyl, aminoacyl, amino protecting group, etc. Among them, the amino protecting group is preferably selected from the group consisting of pivaloyl, tert-butoxycarbonyl, benzyloxycarbonyl, 9-fluorenylmethoxycarbonyl, benzyl, p-methoxybenzyl, allyloxycarbonyl, and trifluoroacetyl, and the like.

The term "tyrosine protein kinase (TPK)" used herein is a type of kinases that catalyze the transfer of the γ-phosphate from adenosine triphosphate (ATP) to tyrosine residue on proteins and that is capable of catalyzing the phosphorylation of tyrosine residue of various protein substrates, and thus have an important effect on cell growth, proliferation and differentiation.

The terms "inhibits", "inhibiting", or "inhibitor" of a kinase, as used herein, refer to inhibition of phosphotransferase activity.

A "metabolite" of a compound disclosed herein is a derivative of that compound that is formed when the compound is metabolized. The term "active metabolite" refers to a biologically active derivative of a compound that is formed when the compound is metabolized. The term "metabolized" as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic acid molecule to aromatic alcohol, aliphatic alcohol, carboxylic acid, amine and free sulfhydryl group. Further information on metabolism may be obtained from *The Pharmacological Basis of Therapeutics*, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites. The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "target protein" refers to a protein molecule or a portion of a protein capable of being bound by a selective binding compound. In certain embodiments, the target protein is tyrosine kinase KIT (wild-type or various mutants or the combination thereof), ABL (wild-type or various mutants or the combination thereof), EGFR (wild-type or various mutants or the combination thereof), FLT3 (wild-type or various mutants or the combination thereof), VEGFR2 (wild-type or various mutants or the combination thereof), RET (wild-type or various mutants or the combination thereof), PDGFRα (wild-type or various mutants or the combination thereof), PDGFRβ (wild-type or various mutants or the combination thereof), BCR/ABL (wild-type or various mutants or the combination thereof), FGFR1 (wild-type or various mutants or the combination thereof), FGFR2 (wild-type or various mutants or the combination thereof), FGFR3 (wild-type or various mutants or the combination thereof), FGFR4 (wild-type or various mutants or the combination thereof).

As used herein, $IC_{50}$ refers to an amount, concentration or dosage of a particular test compound that achieves a 50% inhibition of a maximal response, in an assay that measures such response.

As used herein, $EC_{50}$ refers to a dosage, concentration or amount of a test compound that elicits a dose-dependent response at 50% of maximal expression of a particular response that is induced, provoked or potentiated by the particular test compound.

As used herein, $GI_{50}$ refers to a drug concentration required for growth inhibition of 50% cells, i.e., a drug concentration at which the growth of 50% cells (such as cancer cells) can be inhibited or controlled by the drug.

The Novel Kinase Inhibitor of the Present Invention

The present invention provides a novel kinase inhibitor, comprising a compound of formula (I), or a pharmaceutically acceptable salt, solvate, ester, acid, metabolite or prodrug thereof:

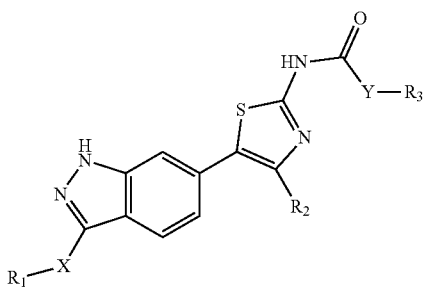

Formula (I)

wherein,

X is $-(CH=CH)_m-$, where m is 0 or 1, and when m is 0, X represents a direct bond;

Y is selected from a group consisting of —NH— or $-(CH_2)_n-$, where n is an integer of 0 to 3, and when n is 0, Y represents a direct bond;

$R_1$ is selected from a group consisting of aryl and heteroaryl groups optionally substituted with 1-3 independent $R_4$ groups;

$R_2$ is selected from a group consisting of hydrogen and $C_{1-6}$ alkyl;

$R_3$ is selected from a group consisting of $C_{1-6}$ alkyl optionally substituted with 1-2 independent $R_5$ groups, $C_{1-6}$ alkylamino, as well as aryl, heteroaryl and heterocyclyl groups optionally substituted with 1-3 independent $R_4$ groups;

$R_4$ is independently selected from a group consisting of halogen, amino, $C_{1-6}$ alkyl, $C_{3-6}$ cycloalkyl, $C_{1-6}$ haloalkyl, $C_{1-6}$ alkoxy, $C_{1-6}$ hydroxyalkyl, $C_{1-6}$ alkylamino, $C_{2-6}$ alkylamide, (4-methylpiperazin-1-yl) methyl, morpholinomethyl, morpholinyl, 4-methylpiperazin-1-yl, 4-piperidyl, and 4-tetrahydropyranyl;

$R_5$ is independently selected from a group consisting of amino, hydroxyl, and $C_{1-6}$ alkylthio.

In a preferred embodiment, X is —(CH=CH)—.

In another preferred embodiment, Y is a direct bond or —CH$_2$—.

In another preferred embodiment, $R_1$ is selected from a group consisting of phenyl, pyridinyl, pyrazolyl, and pyrimidinyl groups optionally substituted with 1-3 independent $R_4$ groups, wherein $R_4$ is independently selected from a group consisting of halogen, amino, $C_{1-6}$ alkyl, $C_{1-6}$ haloalkyl, $C_{1-6}$ alkoxy, and (4-methylpiperazin-1-yl)methyl; $R_1$ is more preferably phenyl, 2-pyridinyl, 3-pyridinyl, 4-pyrazolyl, and 5-pyrimidinyl groups optionally substituted with methyl, amino or halogen; $R_1$ is particularly preferably 2-pyridinyl.

In another preferred embodiment, $R_2$ is hydrogen or methyl.

In another preferred embodiment, $R_3$ is selected from a group consisting of $C_{1-6}$ alkyl optionally substituted with 1-2 independent $R_5$ groups, $C_{1-6}$ alkylamino, as well as phenyl, naphthyl, pyridinyl, piperazinyl and piperidyl groups optionally substituted with 1-3 independent $R_4$ groups, wherein $R_4$ is independently selected from a group consisting of halogen, amino, $C_{1-6}$ alkyl, $C_{1-6}$ haloalkyl, $C_{1-6}$ alkoxy, and (4-methylpiperazin-1-yl)methyl; $R_5$ is independently selected from a group consisting of amino, hydroxyl, and methylthio; $R_3$ is more preferably $C_{1-6}$ alkyl optionally substituted with amino, hydroxy or methylthio; dimethylamino; N-piperazinyl optionally substituted with methyl; phenyl, optionally substituted with halogen, trifluoromethyl or methoxy; naphthyl; 4-pyridinyl; 3-piperidyl; and 4-piperidyl optionally substituted with methyl; $R_3$ is particularly preferably methyl, 2-propyl, 1-amino-3-methylthio-propyl, 1-amino-3-methyl-butyl, methyl-substituted N-piperazinyl, methoxy-substituted phenyl, 4-pyridinyl, or 4-piperidyl.

In a particularly preferred embodiment, when Y is a direct bond, $R_3$ is selected from a group consisting of $C_{1-6}$ alkyl optionally substituted with amino, hydroxy or methylthio, and 4-pyridinyl; and when Y is —CH$_2$—, $R_3$ is selected from a group consisting of phenyl optionally substituted with methoxy, N-piperazinyl optionally substituted with methyl, and 4-piperidyl optionally substituted with methyl.

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

In a preferred embodiment, the inhibitor of the present invention includes the compound of Table 1 as below or a pharmaceutically acceptable salt, solvate, ester, acid, metabolite or prodrug thereof.

TABLE 1
| No. | Compound structure |
|---|---|
| 1 | 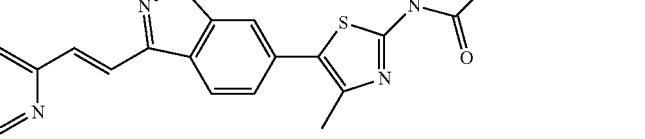 |
| 2 | 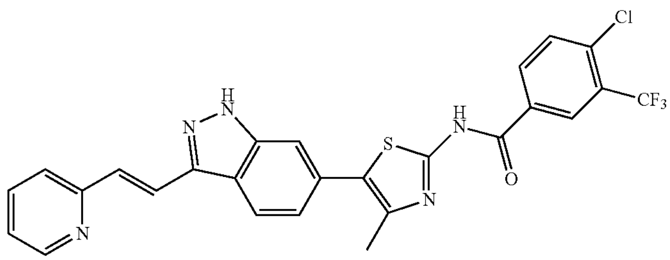 [SMILES: Cc1nc(NC(=O)c2ccc(Cl)c(C(F)(F)F)c2)sc1-c1ccc2c(/C=C/c3ccccn3)n[nH]c2c1] |
| 3 | 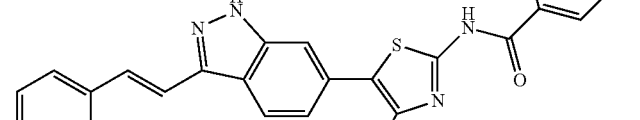 |
| 4 | 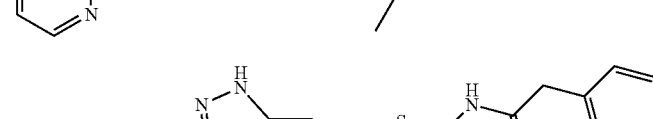 |
| 5 | 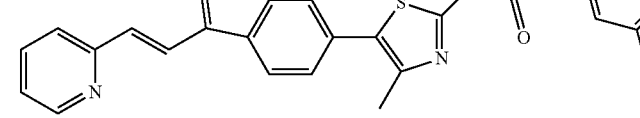 |
| 6 | 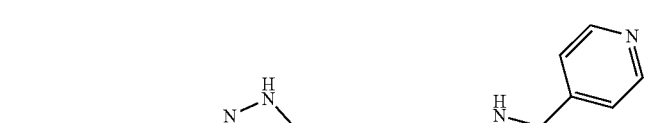 |
| 7 | 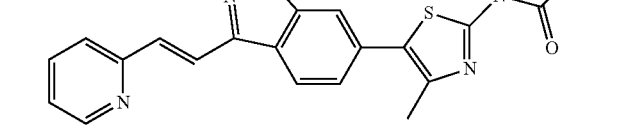 |

TABLE 1-continued

| No. | Compound structure |
|---|---|
| 8 | 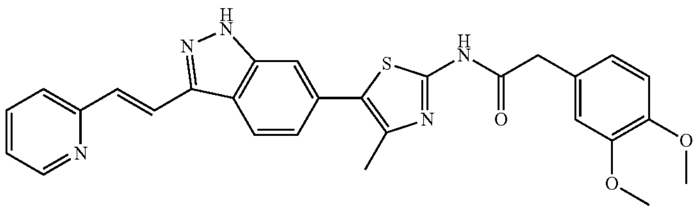 [SMILES: COc1ccc(CC(=O)Nc2nc(C)c(-c3ccc4c(/C=C/c5ccccn5)n[nH]c4c3)s2)cc1OC] |
| 9 | 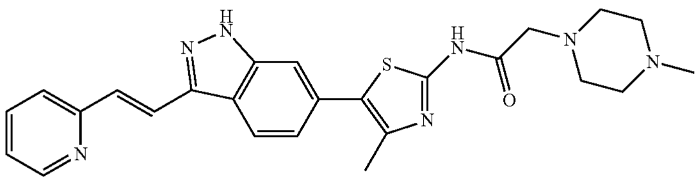 [SMILES: Cc1nc(NC(=O)CN2CCN(C)CC2)sc1-c1ccc2c(/C=C/c3ccccn3)n[nH]c2c1] |
| 10 | 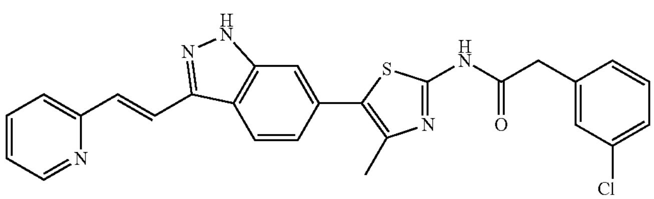 [SMILES: Cc1nc(NC(=O)Cc2cccc(Cl)c2)sc1-c1ccc2c(/C=C/c3ccccn3)n[nH]c2c1] |
| 11 | 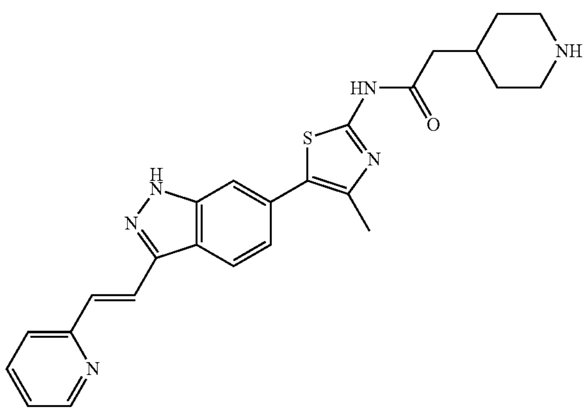 [SMILES: Cc1nc(NC(=O)CC2CCNCC2)sc1-c1ccc2c(/C=C/c3ccccn3)n[nH]c2c1] |
| 12 | 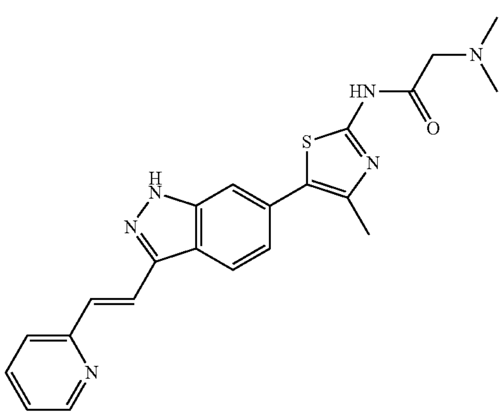 [SMILES: Cc1nc(NC(=O)CN(C)C)sc1-c1ccc2c(/C=C/c3ccccn3)n[nH]c2c1] |

TABLE 1-continued
| No. | Compound structure |
|---|---|
| 13 | 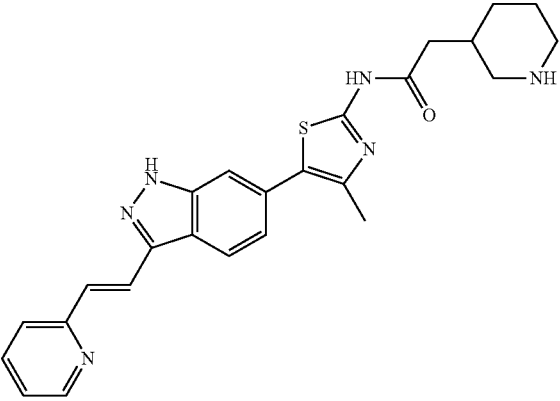 [SMILES: Cc1nc(NC(=O)CC2CCCNC2)sc1-c1ccc2c(/C=C/c3ccccn3)n[nH]c2c1] |
| 14 | 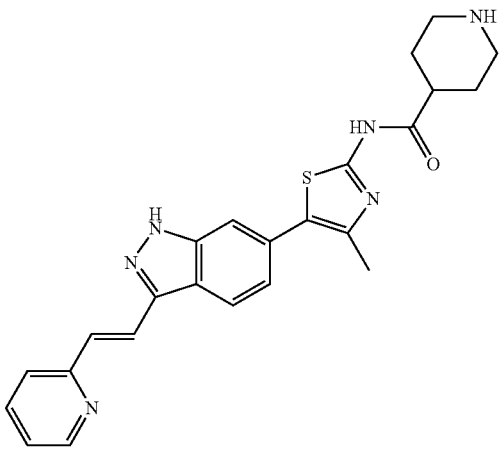 [SMILES: Cc1nc(NC(=O)C2CCNCC2)sc1-c1ccc2c(/C=C/c3ccccn3)n[nH]c2c1] |
| 15 | 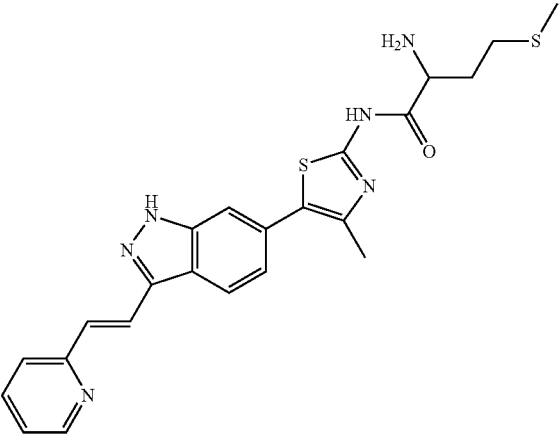 [SMILES: CSCCC(N)C(=O)Nc1nc(C)c(-c2ccc3c(/C=C/c4ccccn4)n[nH]c3c2)s1] |

TABLE 1-continued
| No. | Compound structure |
| --- | --- |
| 16 | 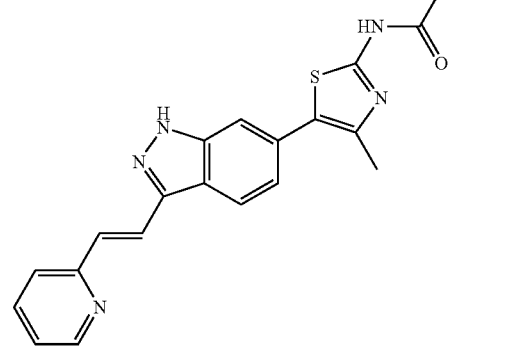 |
| 17 | 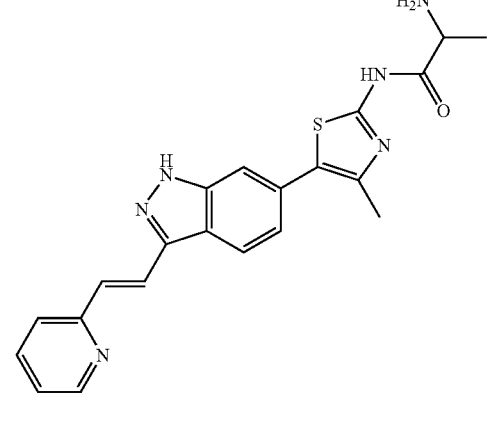 |
| 18 | 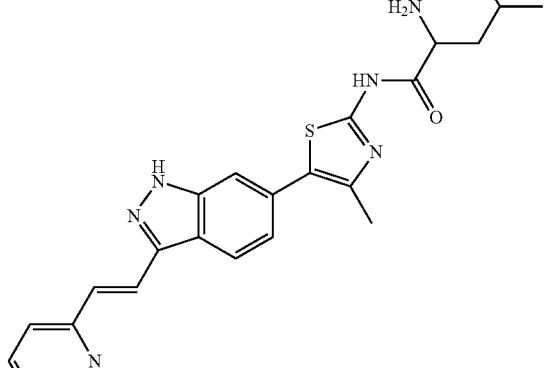 |

TABLE 1-continued

| No. | Compound structure |
|---|---|
| 19 | 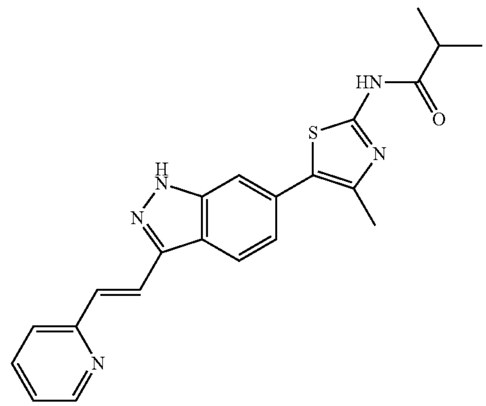 [SMILES: Cc1nc(NC(=O)C(C)C)sc1-c1ccc2c(/C=C/c3ccccn3)n[nH]c2c1] |
| 20 | 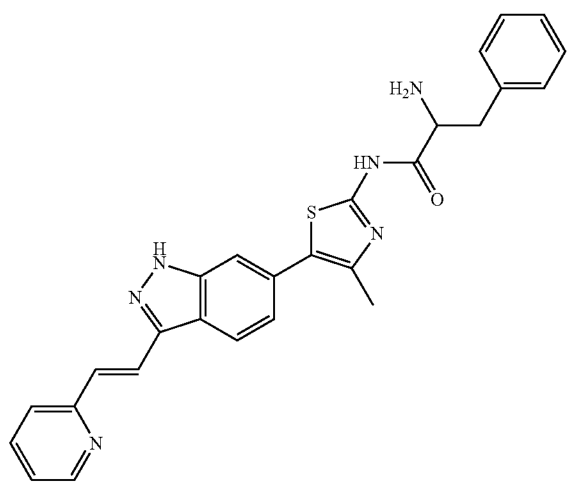 [SMILES: Cc1nc(NC(=O)C(N)Cc2ccccc2)sc1-c1ccc2c(/C=C/c3ccccn3)n[nH]c2c1] |
| 21 | 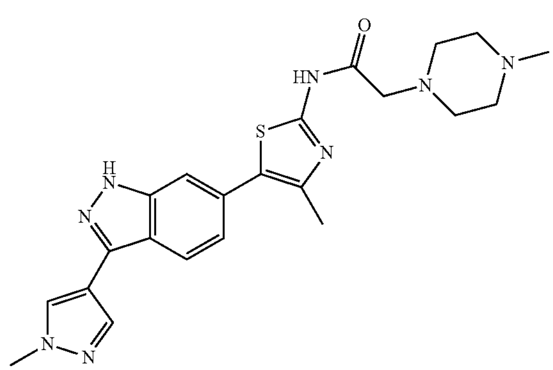 |

TABLE 1-continued
| No. | Compound structure |
|---|---|
| 22 | 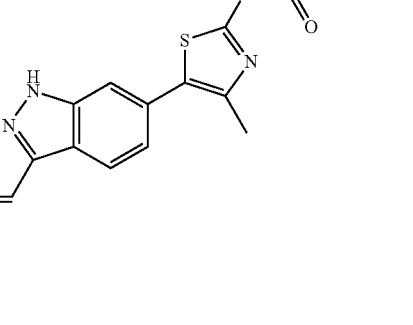 |
| 23 | 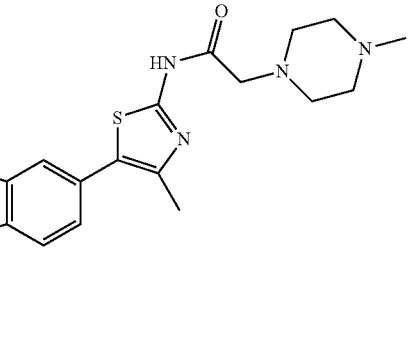 |
| 24 | 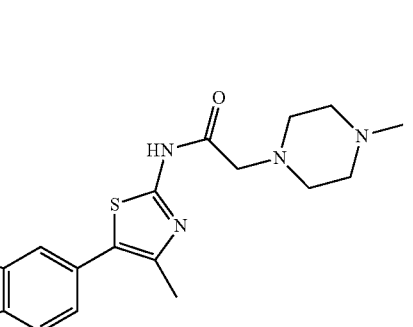 |
| 25 | 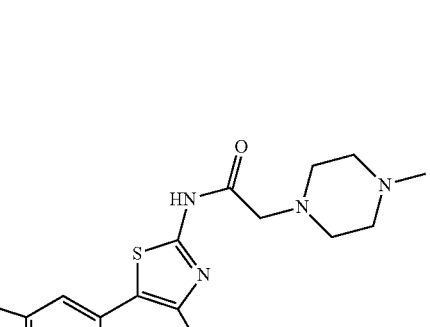 |

TABLE 1-continued
| No. | Compound structure |
|---|---|
| 26 | 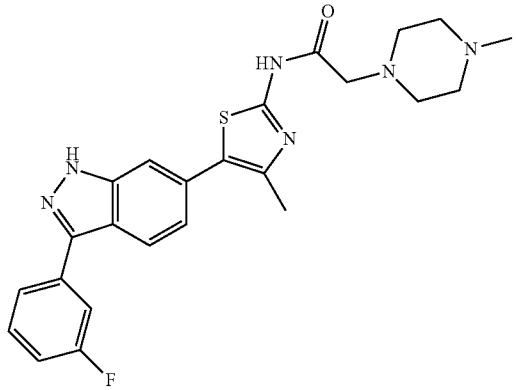 [SMILES: Cc1nc(NC(=O)CN2CCN(C)CC2)sc1-c1ccc2c(-c3cccc(F)c3)n[nH]c2c1] |
| 27 | 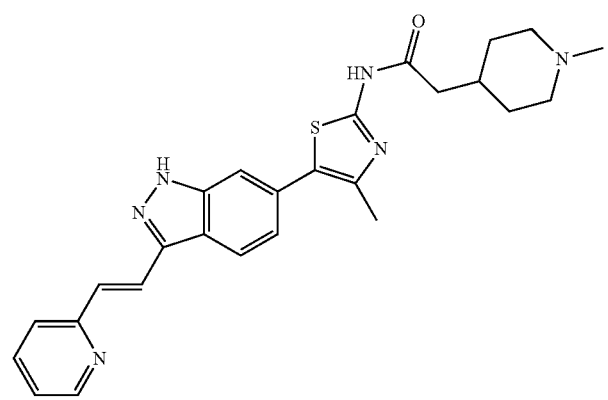 [SMILES: Cc1nc(NC(=O)CC2CCN(C)CC2)sc1-c1ccc2c(/C=C/c3ccccn3)n[nH]c2c1] |
| 28 | 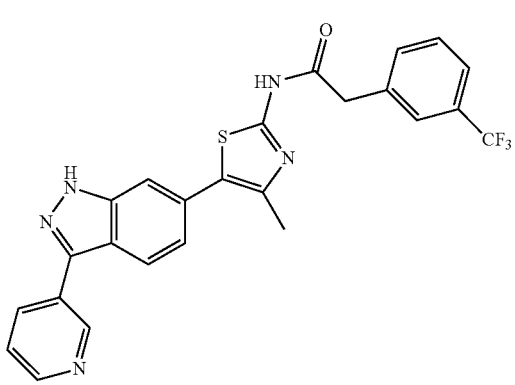 [SMILES: Cc1nc(NC(=O)Cc2cccc(C(F)(F)F)c2)sc1-c1ccc2c(-c3cccnc3)n[nH]c2c1] |
| 29 | 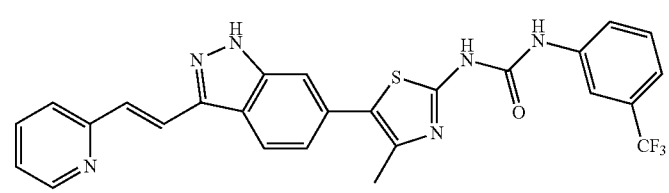 [SMILES: Cc1nc(NC(=O)Nc2cccc(C(F)(F)F)c2)sc1-c1ccc2c(/C=C/c3ccccn3)n[nH]c2c1] |

TABLE 1-continued

| No. | Compound structure |
|---|---|
| 30 | (structure shown) |

Described herein is a novel kinase inhibitor. The pharmaceutically acceptable salts, solvates, esters, acids, pharmaceutically active metabolites and prodrugs of these compounds are also described herein.

In additional or further embodiments, the compounds described herein are metabolized upon administration to an organism in need thereof to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable inorganic acid such as hydrochloric acid, hydrobromic acid, sulfuric acid, nitric acid, phosphoric acid, metaphosphoric acid, and the like; or with an organic acid such as acetic acid, propionic acid, hexanoic acid, cyclopentanepropionic acid, glycolic acid, pyruvic acid, lactic acid, malonic acid, malic acid, citric acid, succinic acid, maleic acid, tartaric acid, fumaric acid, trifluoroacetic acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 4-methylbicyclo-[2.2.2] oct-2-ene-1-carboxylic acid, 2-naphthalenesulfonic acid, tertiary butylacetic acid, glucoheptonic acid, 4,4'-methylenebis-(3-hydroxy-2-ene-1-carboxylic acid), 3-phenylpropionic acid, trimethylacetic acid, lauryl sulfuric acid, gluconic acid, glutamic acid, salicylic acid, hydroxynaphthoic acid, stearic acid, muconic acid, and the like; (2) base addition salts formed when an acidic proton present in the parent compound either is replaced by a metal ion, e.g., an alkali metal ion (e.g. lithium, sodium, potassium), an alkaline earth metal ion (e.g. magnesium, or calcium), or an aluminum ion; or coordinates with an organic base or an inorganic base, acceptable organic bases include ethanolamine, diethanolamine, triethanolamine, trimethylamine, N-methylglucamine, and the like; acceptable inorganic bases include aluminum hydroxide, calcium hydroxide, potassium hydroxide, sodium carbonate, sodium hydroxide, and the like.

The corresponding counterions of the pharmaceutically acceptable salts may be analyzed and identified using various methods including, but not limited to, ion exchange chromatography, ion chromatography, capillary electrophoresis, inductively coupled plasma, atomic absorption spectroscopy, mass spectrometry, or any combination thereof.

The salts are recovered by using at least one of the following techniques: filtration, precipitation with a nonsolvent followed by filtration, evaporation of the solvent, or, in the case of aqueous solutions, lyophilization.

The screening and characterization of the pharmaceutically acceptable salts, polymorphs and/or solvates may be accomplished using a variety of techniques including, but not limited to, thermal analysis, x-ray diffraction, spectroscopy, microscopy, and element analysis. The various spectroscopic techniques used include, but are not limited to, Raman, FTIR, UVIS, and NMR (liquid and solid state). The various microscopy techniques include, but are not limited to, IR microscopy and Raman microscopy.

The Pharmaceutical Composition of the Present Invention

The present invention also provides a pharmaceutical composition comprising at least one compound of formula (I), or a pharmaceutically acceptable salt, solvate, ester, acid, pharmaceutically active metabolite or prodrug of the compound, and and a pharmaceutically acceptable carrier or excipient, as well as optionally other therapeutic agents.

In the course of treatment, it may be used alone or in combination with one or more other therapeutic agents. The medicament comprising a compound of the invention may be administered to a patient through at least one of injection, oral, inhalation, rectal and transdermal administration. Other therapeutic agents may be selected from the following: immunosuppressants (e.g., tacrolimus, cyclosporin, rapamycin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), allergy vaccines, antihistamines, antileukotrienes, β-agonists, theophylline, anticholinergics, or other selective kinase inhibitors (e.g., mTOR inhibitors, c-Met inhibitors) or her2 antibodies. In addition, the other therapeutic agents may also be Rapamycin, Crizotinib, Tamoxifen, Raloxifene, Anastrozole, Exemestane, Letrozole, Herceptin™ (Trastuzumab), Gleevec™ (Imatinib), Taxol™

(Paclitaxel), Cyclophosphamide, Lovastatin, Minosine, Cytarabine, 5-Fluorouracil (5-FU), Methotrexate (MTX), Taxotere™ (Docetaxel), Zoladex™ (Goserelin), Vincristine, Vinblastine, Nocodazole, Teniposide, Etoposide, Gemzar™ (Gemcitabine), Epothilone, Navelbine, Camptothecin, Daunonibicin, Dactinomycin, Mitoxantrone, Amsacrine, Doxorubicin (Adriamycin), Epirubicin or Idarubicin. Alternatively, other therapeutic agents may be cytokines such as G-CSF (Granulocyte-Colony Stimulating Factor). Alternatively, other therapeutic agents may be for example, but are not limited to, CMF (Cyclophosphamide, Methotrexate and 5-Fluorouracil), CAF (Cyclophosphamide, Adriamycin and 5-Fluorouracil), AC (Adriamycin and Cyclophosphamide), FEC (5-Fluorouracil, Epirubicin and Cyclophosphamide), ACT or ATC (Adriamycin, Cyclophosphamide and Paclitaxel) or CMFP (Cyclophosphamide, Methotrexate, 5-Fluorouracil and Prednisone).

In the embodiments of the invention, when a patient is treated in accordance with the invention, the amount of a given agent will vary depending upon factors such as the particular dosing regimen, the type of the disease or condition and its severity, the identity (e.g., weight) of the subject or host in need of treatment, but can be routinely determined in a manner known in the art according to the particular circumstances surrounding the case, including, e.g., the specific agent being administered, the route of administration, the condition being treated, and the subject or host being treated. In general, doses employed for adult human treatment will typically be in the range of 0.02-5000 mg per day, such as from about 1-1500 mg per day. The desired dose may conveniently be presented in a single dose or as divided doses administered simultaneously (or over a short period of time) or at appropriate intervals, for example as two, three, four or more sub-doses per day. It will be appreciated by those skilled in the art that, although the above dosage ranges are given, the specific effective amounts may be appropriately adjusted depending on the condition of the patient and the judgment of the practitioner.

Use of Medicines of the Present Invention

The kinase inhibitor of the present invention comprises a compound of formula (I), or a pharmaceutically acceptable salt, solvate, ester, acid, metabolite or prodrug thereof, or the pharmaceutical composition, used for reducing or inhibiting the kinase activity of cKIT (especially mutant cKIT/T670I), FLT3 (including mutant FLT3-ITD), PDGFRα, PDGFRβ, and/or VEGFR2 in cells or subjects, and/or preventing or treating a disorder related to the activity of cKIT (especially mutant cKIT/T670I), FLT3 (including mutant FLT3-ITD), PDGFRα, PDGFRβ, and/or VEGFR2 in subjects.

The compound of formula (I), or a pharmaceutically acceptable salt, solvate, ester, acid, metabolite or prodrug thereof, or the pharmaceutical composition may be used for the treatment, prevention or amelioration of one or more diseases selected from a group consisting of: solid tumors (including benign or especially malignant types), especially sarcoma, Gastrointestinal Stromal Tumors (GIST), colorectal cancer, Acute Myeloblastic Leukemia (AML), Chronic Myelogenous Leukemia (CML), neoplasia, thyroid carcinoma, systemic mastocytosis, eosinophilia syndrome, fibrosis, lupus erythematosus, graft versus host disease, neurofibromatosis, pulmonary hypertension, Alzheimer's disease, seminoma, dysgerminoma, mast cell tumors, lung cancer, bronchial carcinoma, testicular intraepithelial neoplasia, melanoma, breast cancer, neuroblastoma, papillary/follicular thyroid carcinoma, malignant lymphoma, non-Hodgkin's lymphoma, multiple endocrine neoplasia type 2, pheochromocytoma, thyroid carcinoma, parathyroid hyperplasia/adenoma, colon cancer, colorectal adenoma, ovarian cancer, prostate cancer, glioblastoma, brain tumor, malignant glioma, pancreatic cancer, malignant pleural endothelioma, hemangioblastoma, hemangioma, kidney cancer, liver cancer, adrenal carcinoma, bladder cancer, stomach cancer, rectal cancer, vaginal cancer, cervical cancer, endometrial cancer, multiple myeloma, neck and head tumors, as well as other proliferative conditions, or the like, or the combination thereof. It is especially preferred for the treatment of Gastrointestinal Stromal Tumors (GIST), colorectal cancer, Acute Myeloblastic Leukemia (AML), Chronic Myelogenous Leukemia (CML), thyroid carcinoma, or the like, or the combination thereof. Most preferably, the inhibitor of the present invention or the pharmaceutical composition thereof can be used for the treatment or prevention of gastrointestinal stromal tumors, especially cKIT-T670I mutant gastrointestinal stromal tumors.

The compound of formula (I), or a pharmaceutically acceptable salt, solvate, ester, acid, metabolite or prodrug thereof, or the pharmaceutical composition may be used for the treatment, prevention or amelioration of the autoimmune disease selected from a group consisting of: arthritis, rheumatic arthritis, osteoarthritis, lupus, rheumatoid arthritis, inflammatory bowel disease, psoriatic arthritis, osteoarthritis, Still's disease, Juvenile arthritis, diabetes, myasthenia gravis, Hashimoto's thyroiditis, Ord's hyroiditis, Graves' disease, Sjögren's syndrome, multiple sclerosis, Guillain-Barré syndrome, acute disseminated encephalomyelitis, Addison's disease, Opsoclonus-Myoclonus-Ataxia, ankylosing spondylitis, antiphospholipid syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm-type autoimmune hemolytic anemia, Wegener's granulomatosis, psoriasis, alopecia universalis, Behcet's disease, chronic fatigue, Familial dysautonomia, endometriosis, interstitial cystitis, neuromyotonia, scleroderma or vulvodynia.

Preparation of the Compound

Compounds of formula (I) may be synthesized using standard synthetic techniques known to those of skill in the art or using methods known in the art in combination with methods described herein. In additions, solvents, temperatures and other reaction conditions presented herein may vary according to those of skill in the art. As a further guide the following synthetic methods may also be utilized.

The reactions can be employed in a linear sequence to provide the compounds described herein or they may be used to synthesize fragments which are subsequently joined by the methods described herein and/or known in the art.

In certain embodiments, provided herein are methods of making and methods of using kinase inhibitor compounds described herein. In certain embodiments, compounds described herein can be synthesized using the following synthetic schemes. Compounds may be synthesized using methodologies analogous to those described below by the use of appropriate alternative starting materials.

The starring materials used for the synthesis of the compounds described herein may be synthesized or can be obtained from commercial sources. The compounds described herein and other related compounds having different substituents can be synthesized using techniques and materials known to those of skill in the art. General methods for the preparation of compounds as disclosed herein may be derived from known reactions in the field, and the reactions may be modified by the use of appropriate reagents and conditions, as would be recognized by the skilled person, for the introduction of the various moieties into the molecules as provided herein.

The products of the reactions may be isolated and purified, if desired, using conventional techniques, including, but not limited to, filtration, distillation, crystallization, chromatography and the like. Such products may be characterized using conventional means, including physical A non-limiting example of a synthetic approach towards the preparation of compounds of formula (I) is shown in the following synthetic routes.

Example 1: (E)-N-(4-methyl-5-(3-(2-(pyridin-2-yl)vinyl)-1H-indazol-6-yl)thiazol-2-yl)-4-((4-methylpiperazin-1-yl)methyl)benzamide

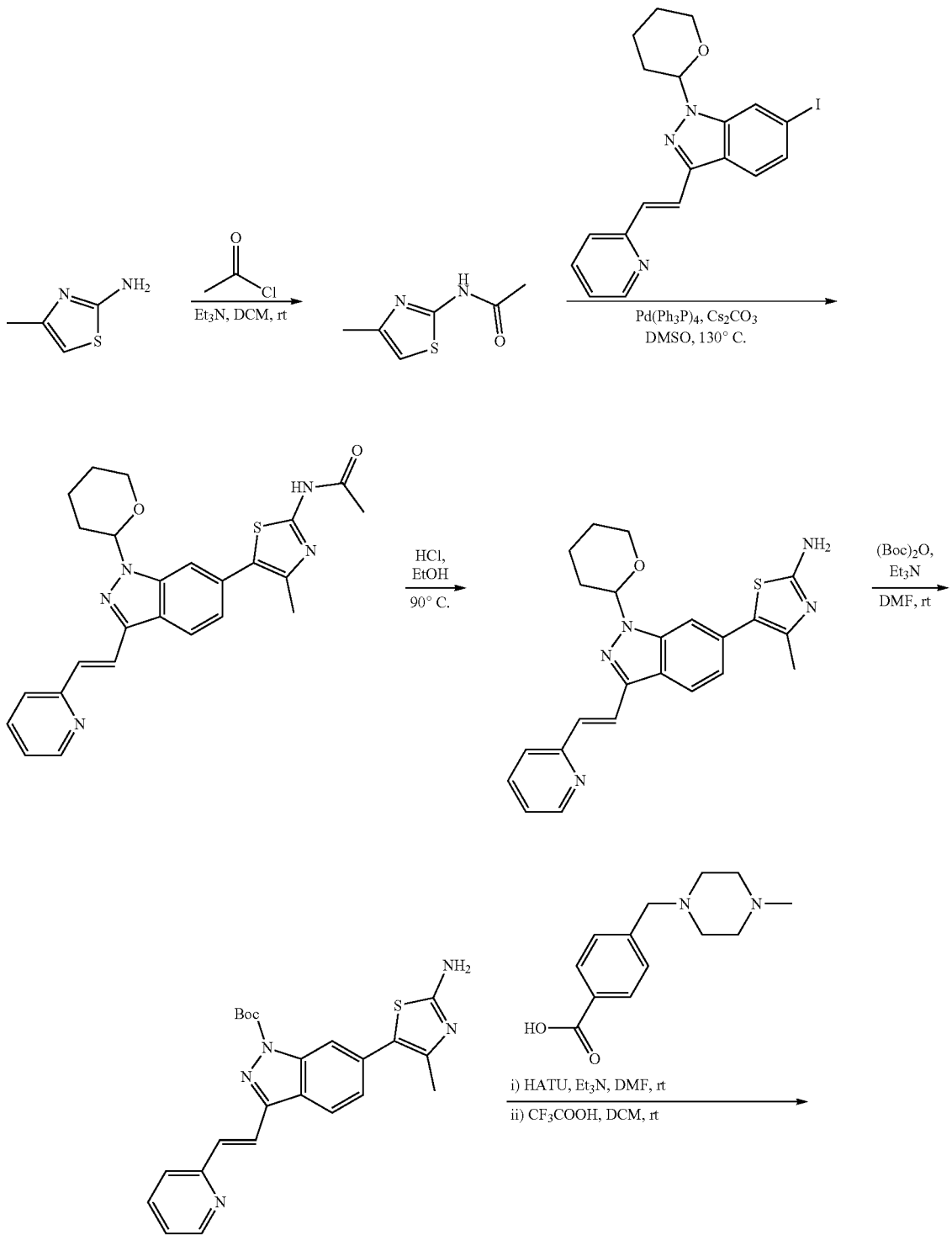

-continued

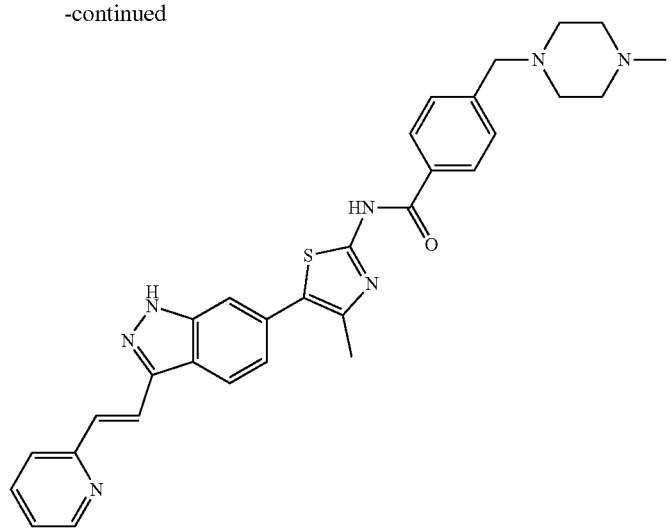

1

N-(4-methylthiazol-2-yl)acetamide: 4-methylthiazol-2-amine (2 g) was added to a 100 mL round bottom flask, then anhydrous dichloromethane (50 mL), triethylamine (3.9 mL) were added, and acetyl chloride (1.5 mL) was dropwise added slowly. The reaction system was reacted for 4 hours under the gas argon protection at room temperature. After the reaction, the solvent in the system was dried by distillation under reduced pressure and the resultant was neutralized with saturated sodium bicarbonate to pH>10, and then extracted with ethyl acetate. The organic phase was washed with water and saturated saline solution respectively, and then dried with anhydrous sodium sulfate. The organic phase was filtered and dried by distillation under reduced pressure to obtain a crude product. The crude product was purified by pressurized silica gel column chromatography to obtain a pure product, MS (ESI) m/z (M+1)+: 157.05.

(E)-N-(4-methyl-5-(3-(2-(pyridin-2-yl)vinyl)-1-(tetrahydro-2H-pyran-2-yl)-1H-indazol-6-yl)thiazol-2-yl)acetamide: N-(4-methylthiazol-2-yl)acetamide (1.0 g) was added in a round bottom flask, and then dimethyl sulfoxide (20 mL), (E)-6-iodo-3-(2-(pyridin-2-yl)vinyl)-1-(tetrahydro-2H-pyran-2-yl)-1H-indazole (3.1 g), palladium tetrakistriphenylphosphine (0.37 g) and cesium carbonate (6.2 g) were added. The reaction system was heated to 130° C. and reacted for 14 hours under the gas argon protection. After the reaction, the solvent in the system was dried by distillation under reduced pressure, and the resultant was diluted with water and extracted with ethyl acetate. The organic phase was washed with water and saturated saline solution respectively, and then dried with anhydrous sodium sulfate. The organic phase was filtered and dried by distillation under reduced pressure to obtain a crude product. The crude product was purified by pressurized silica gel column chromatography to obtain a pure product, MS (ESI) m/z (M+1)+: 460.18.

(E)-4-methyl-5-(3-(2-(pyridin-2-yl)vinyl)-1H-indazol-6-yl)thiazol-2-amine: (E)-N-(4-methyl-5-(3-(2-(pyridin-2-yl)vinyl)-1-(tetrahydro-2H-pyran-2-yl)-1H-indazol-6-yl)thiazol-2-yl)acetamide (2.0 g), ethanol (20 mL) and 6 mol/liter hydrochloric acid (15 mL) were added in a 100 mL round bottom flask. The reaction system was heated to 90° C. and reacted for 14 hours under the gas argon protection. After the reaction, the solvent in the system was dried by distillation under reduced pressure and the resultant was neutralized with saturated sodium bicarbonate to pH>10, and then a solid precipitated out and was filtered to obtain a crude product. The crude product was washed with ethyl acetate to obtain a pure product, MS (ESI) m/z (M+1)+: 334.11.

Tert-butyl(E)-6-(2-amino-4-methylthiazol-5-yl)-3-(2-(pyridin-2-yl)vinyl)-1H-indazole-1-carboxamide: (E)-4-methyl-5-(3-(2-(pyridin-2-yl)vinyl)-1H-indazol-6-yl)thiazol-2-amine (1 g) was added to a 50 mL round bottom flask, and then anhydrous N,N-dimethylformamide (10 mL), triethylamine (0.9 mL), and di-tert-butyl dicarbonate (1.0 g) were added. The reaction system was reacted for 4 hours under the gas argon protection at room temperature. After the reaction, the solvent in the system was dried by distillation under reduced pressure and the resultant was neutralized with saturated sodium bicarbonate to pH>10, and then the aqueous phase was extracted with ethyl acetate. The organic phase was washed with water and saturated saline solution respectively, and then dried with anhydrous sodium sulfate. The organic phase was filtered and dried by distillation under reduced pressure to obtain a crude product. The crude product was purified by pressurized silica gel column chromatography to obtain a pure product, MS (ESI) m/z (M+1)+: 434.17.

(E)-N-(4-methyl-5-(3-(2-(pyridin-2-yl)vinyl)-1H-indazol-6-yl)thiazol-2-yl)-4-((4-methylpiperazin-1-yl)methyl)benzamide (1): Tert-butyl(E)-6-(2-amino-4-methylthiazol-5-yl)-3-(2-(pyridin-2-yl)vinyl)-1H-indazole-1-carboxamide (0.05 g) was added to a round bottom flask, and then N,N-dimethylformamide (5 mL), 4-((4-methylpiperazin-1-yl)methyl)benzoic acid (0.03 g), 2-(7-benzotriazole oxide)-N,N,N',N'-tetramethylurea hexafluorophosphate (0.07 g) and triethylamine (0.03 mL) were added. The reaction system was stirred for 14 hours under the gas argon protection at room temperature. After the reaction, the solvent in the system was dried by distillation under reduced pressure, and the resultant was diluted with water and extracted with ethyl acetate. The organic phase was washed with water and saturated saline solution respectively, and then dried with anhydrous sodium sulfate. The organic phase was filtered and dried by distillation under reduced pressure to obtain a crude product.

The crude product was dissolved in anhydrous dichloromethane (2 mL), and trifluoro acetic acid (1 mL) was added. The reaction system was stirred for 14 hours under the gas argon protection at room temperature. After the reaction, the solvent in the system was dried by distillation under reduced pressure, and the resultant was diluted with water and neutralized with saturated sodium bicarbonate solution to pH>10. The aqueous phase was extracted with ethyl acetate, and the organic phase was washed with water and saturated saline solution respectively, and then dried with anhydrous sodium sulfate. The organic phase was filtered and dried by distillation under reduced pressure to obtain a crude product. The crude product was purified by pressurized silica gel column chromatography to obtain Compound 1, MS (ESI) m/z (M+1)+: 550.24.

Example 2: (E)-4-chloro-N-(4-methyl-5-(3-(2-(pyridin-2-yl)vinyl)-1H-indazol-6-yl)thiazol-2-yl)-3-(trifluoromethyl)benzamide

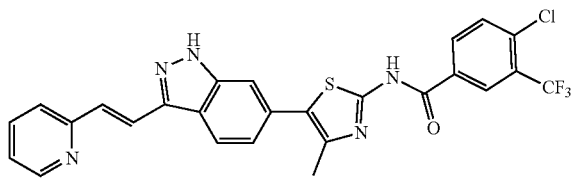 [SMILES: Cc1nc(NC(=O)c2ccc(Cl)c(C(F)(F)F)c2)sc1-c1ccc2c(/C=C/c3ccccn3)n[nH]c2c1]

The synthesis of Example 2 was done using steps similar to those described in Example 1. MS (ESI) m/z (M+1)+: 540.09.

Example 3: (E)-N-(4-methyl-5-(3-(2-(pyridin-2-yl)vinyl)-1H-indazol-6-yl)thiazol-2-yl)-2-(3-(trifluoromethyl)phenyl)acetamide

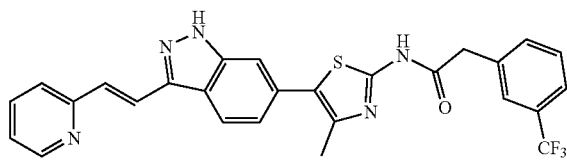

The synthesis of Example 3 was done using steps similar to those described in Example 1. MS (ESI) m/z (M+1)+: 520.14.

Example 4: (E)-N-(4-methyl-5-(3-(2-(pyridin-2-yl)vinyl)-1H-indazol-6-yl)thiazol-2-yl) isonicotinamide

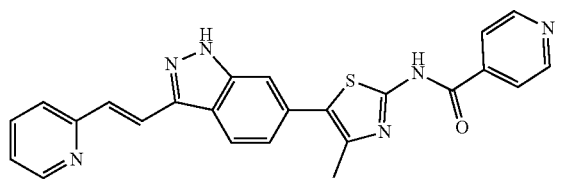 [SMILES: Cc1nc(NC(=O)c2ccncc2)sc1-c1ccc2c(/C=C/c3ccccn3)n[nH]c2c1]

The synthesis of Example 4 was done using steps similar to those described in Example 1. MS (ESI) m/z (M+1)+: 439.14.

Example 5: (E)-N-(5-(3-(2-(pyridin-2-yl)vinyl)-1H-indazol-6-yl)thiazol-2-yl)acetamide

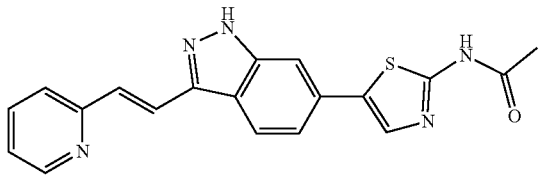 [SMILES: CC(=O)Nc1ncc(-c2ccc3c(/C=C/c4ccccn4)n[nH]c3c2)s1]

The synthesis of Example 5 was done using steps similar to those described in Example 1. MS (ESI) m/z (M+1)+: 361.11.

Example 6: (E)-N-(4-methyl-5-(3-(2-(pyridin-2-yl)vinyl)-1H-indazol-6-yl)thiazol-2-yl)-3-(trifluoromethyl)benzamide

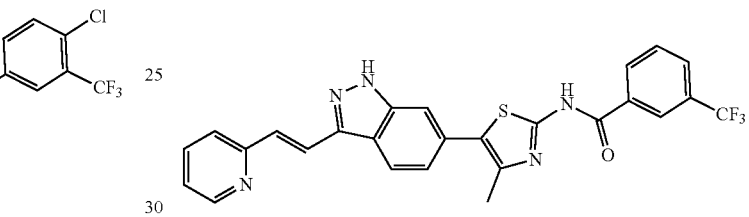

The synthesis of Example 6 was done using steps similar to those described in Example 1. MS (ESI) m/z (M+1)+: 506.13.

Example 7: (E)-N-(4-methyl-5-(3-(2-(pyridin-2-yl)vinyl)-1H-indazol-6-yl)thiazol-2-yl)-2-(naphthalene-1-yl)acetamide

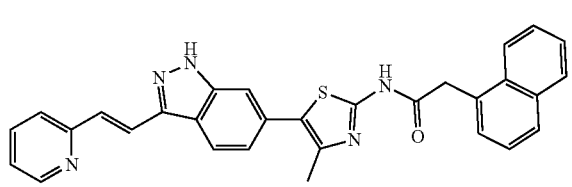 [SMILES: Cc1nc(NC(=O)Cc2cccc3ccccc23)sc1-c1ccc2c(/C=C/c3ccccn3)n[nH]c2c1]

The synthesis of Example 7 was done using steps similar to those described in Example 1. MS (ESI) m/z (M+1)+: 502.17.

Example 8: (E)-2-(3,4-methoxyphenyl)-N-(4-methyl-5-(3-(2-(pyridin-2-yl)vinyl)-1H-indazol-6-yl)thiazol-2-yl)acetamide

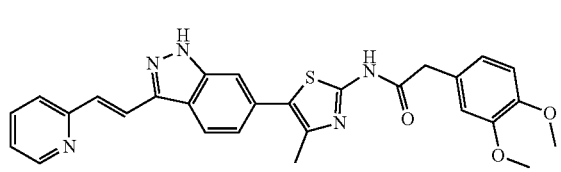 [SMILES: COc1ccc(CC(=O)Nc2nc(C)c(-c3ccc4c(/C=C/c5ccccn5)n[nH]c4c3)s2)cc1OC]

The synthesis of Example 8 was done using steps similar to those described in Example 1. MS (ESI) m/z (M+1)+: 512.18.

Example 9: (E)-N-(4-methyl-5-(3-(2-(pyridin-2-yl)vinyl)-1H-indazol-6-yl)thiazol-2-yl)-2-(4-methylpiperazin-1-yl)acetamide

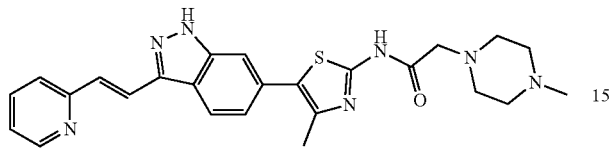

The synthesis of Example 9 was done using steps similar to those described in Example 1. MS (ESI) m/z (M+1)+: 474.21.

Example 10: (E)-2-(3-chloro phenyl)-N-(4-methyl-5-(3-(2-(pyridin-2-yl)vinyl)-1H-indazol-6-yl)thiazol-2-yl)acetamide

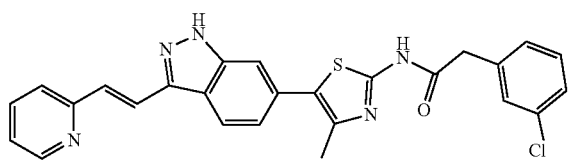 [SMILES: Cc1nc(NC(=O)Cc2cccc(Cl)c2)sc1-c1ccc2c(/C=C/c3ccccn3)n[nH]c2c1]

The synthesis of Example 10 was done using steps similar to those described in Example 1. MS (ESI) m/z (M+1)+: 486.12.

Example 11: (E)-N-(4-methyl-5-(3-(2-(pyridin-2-yl)vinyl)-1H-indazol-6-yl)thiazol-2-yl)-2-(piperidin-4-yl)acetamide

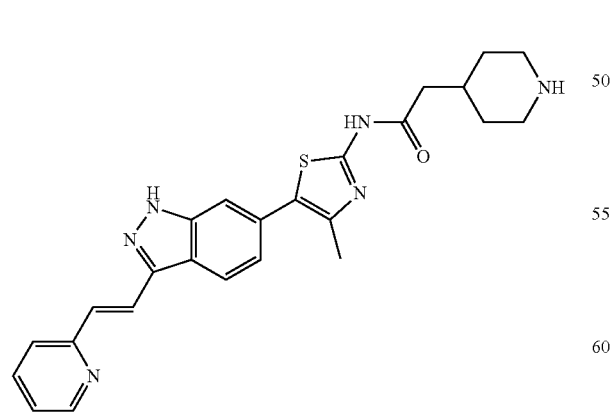

The synthesis of Example 11 was done using steps similar to those described in Example 1. MS (ESI) m/z (M+1)+: 459.20.

Example 12: (E)-2-(dimethylamino)-N-(4-methyl-5-(3-(2-(pyridin-2-yl)vinyl)-1H-indazol-6-yl)thiazol-2-yl)acetamide

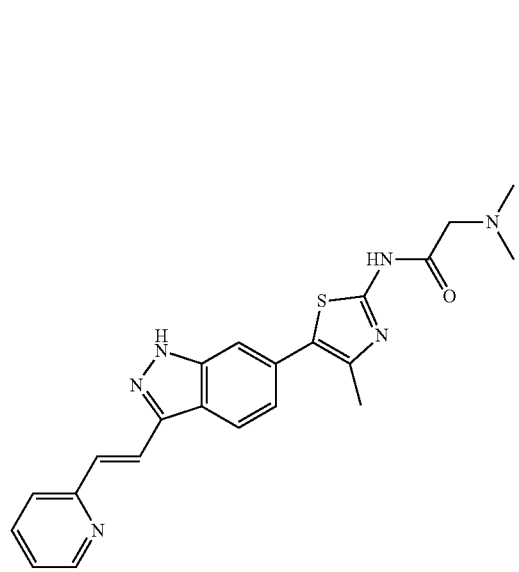 [SMILES: Cc1nc(NC(=O)CN(C)C)sc1-c1ccc2c(/C=C/c3ccccn3)n[nH]c2c1]

The synthesis of Example 12 was done using steps similar to those described in Example 1. MS (ESI) m/z (M+1)+: 419.17.

Example 13: (E)-N-(4-methyl-5-(3-(2-(pyridin-2-yl)vinyl)-1H-indazol-6-yl)thiazol-2-yl)-2-(piperidin-3-yl)acetamide

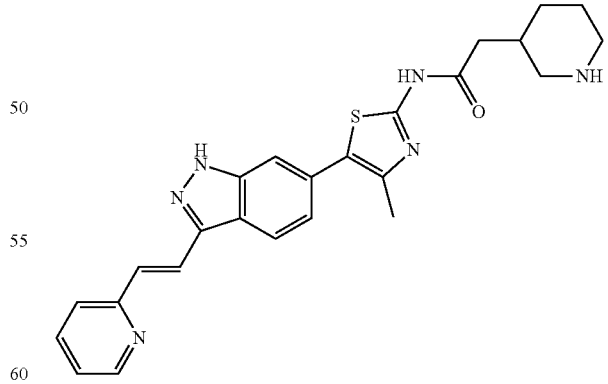

The synthesis of Example 13 was done using steps similar to those described in Example 1. MS (ESI) m/z (M+1)+: 459.20.

Example 14: (E)-N-(4-methyl-5-(3-(2-(pyridin-2-yl)vinyl)-1H-indazol-6-yl)thiazol-2-yl) piperidin-4-carboxamide

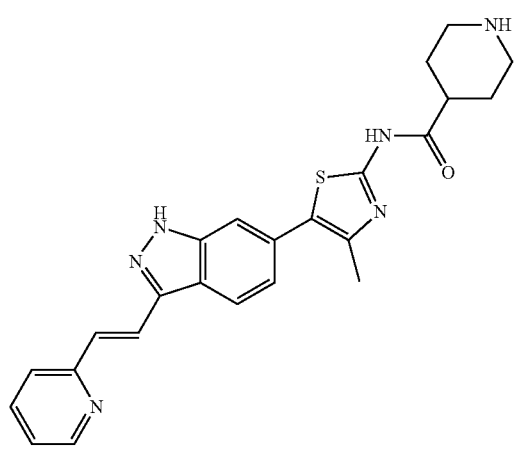 [SMILES: Cc1nc(NC(=O)C2CCNCC2)sc1-c1ccc2c(/C=C/c3ccccn3)n[nH]c2c1]

The synthesis of Example 14 was done using steps similar to those described in Example 1. MS (ESI) m/z (M+1)+: 445.18.

Example 15: (E)-2-amino-N-(4-methyl-5-(3-(2-(pyridin-2-yl)vinyl)-1H-indazol-6-yl)thiazol-2-yl)-4-(methylthio)butanamide

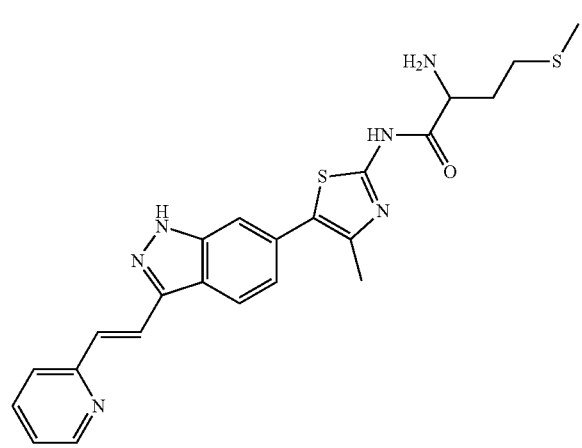 [SMILES: CSCCC(N)C(=O)Nc1nc(C)c(-c2ccc3c(/C=C/c4ccccn4)n[nH]c3c2)s1]

The synthesis of Example 15 was done using steps similar to those described in Example 1. MS (ESI) m/z (M+1)+: 465.16.

Example 16: (E)-1-methyl-N-(4-methyl-5-(3-(2-(pyridin-2-yl)vinyl)-1H-indazol-6-yl)thiazol-2-yl) piperidin-4 carboxamide

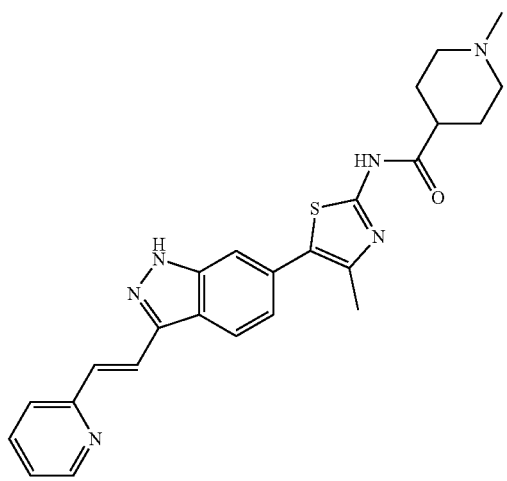 [SMILES: Cc1nc(NC(=O)C2CCN(C)CC2)sc1-c1ccc2c(/C=C/c3ccccn3)n[nH]c2c1]

The synthesis of Example 16 was done using steps similar to those described in Example 1. MS (ESI) m/z (M+1)+: 458.20.

Example 17: (E)-2-amino-N-(4-methyl-5-(3-(2-(pyridin-2-yl)vinyl)-1H-indazol-6-yl)thiazol-2-yl) propionamide

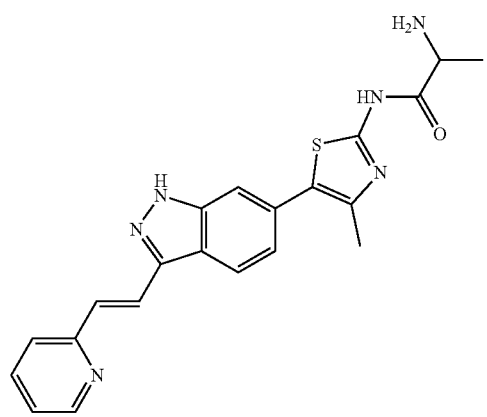 [SMILES: Cc1nc(NC(=O)C(C)N)sc1-c1ccc2c(/C=C/c3ccccn3)n[nH]c2c1]

The synthesis of Example 17 was done using steps similar to those described in Example 1. MS (ESI) m/z (M+1)+: 405.15.

Example 18: (E)-2-amino-4-methyl-N-(4-methyl-5-(3-(2-(pyridin-2-yl)vinyl)-1H-indazol-6-yl)thiazol-2-yl)pentanamide

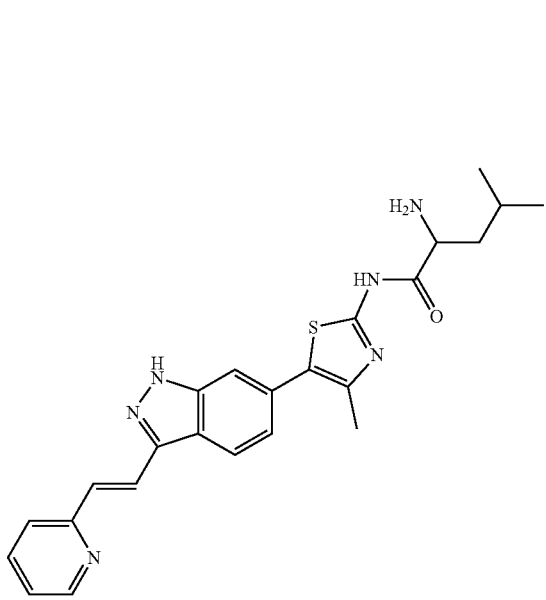 [SMILES: Cc1nc(NC(=O)C(N)CC(C)C)sc1-c1ccc2c(/C=C/c3ccccn3)n[nH]c2c1]

The synthesis of Example 18 was done using steps similar to those described in Example 1. MS (ESI) m/z (M+1)+: 447.20.

Example 19: (E)-N-(4-methyl-5-(3-(2-(pyridin-2-yl)vinyl)-1H-indazol-6-yl)thiazol-2-yl) isobutanamide

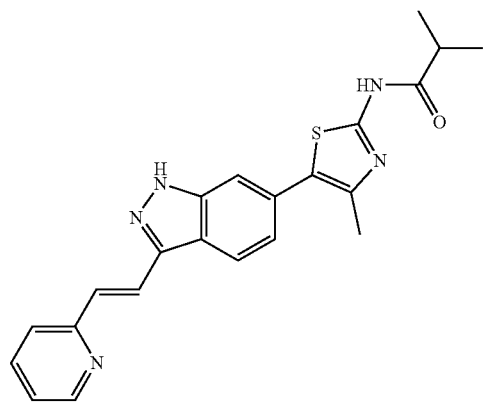 [SMILES: Cc1nc(NC(=O)C(C)C)sc1-c1ccc2c(/C=C/c3ccccn3)n[nH]c2c1]

The synthesis of Example 19 was done using steps similar to those described in Example 1. MS (ESI) m/z (M+1)+: 404.16.

Example 20: (E)-2-amino-N-(4-methyl-5-(3-(2-(pyridin-2-yl)vinyl)-1H-indazol-6-yl)thiazol-2-yl)-3-phenylpropionamide

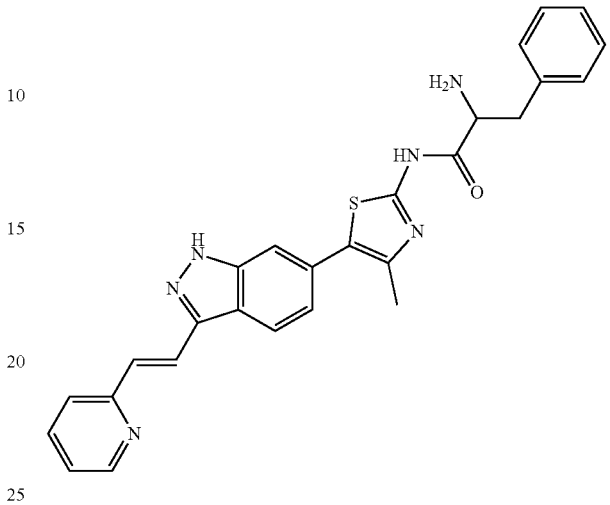

The synthesis of Example 20 was done using steps similar to those described in Example 1. MS (ESI) m/z (M+1)+: 481.18.

Example 21: N-(4-methyl-5-(3-(1-methyl-1H-pyrazol-4-yl)-1H-indazol-6-yl)thiazol-2-yl)-2-(4-methylpiperazin-1-yl)acetamide

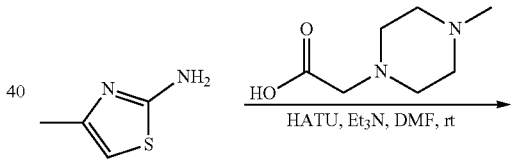

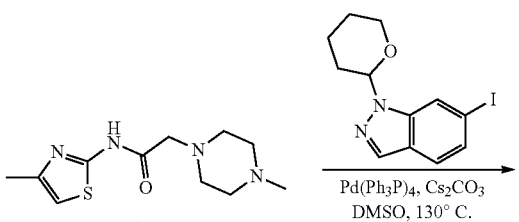

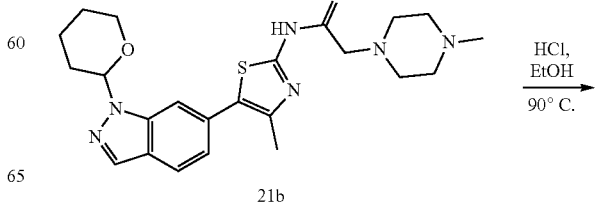

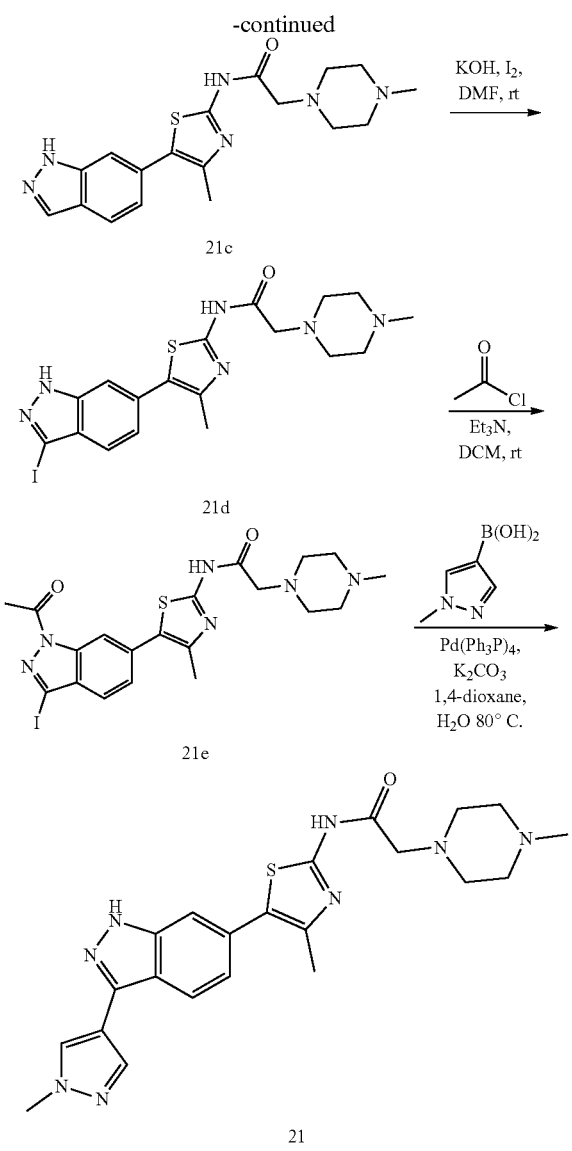

2-(4-methylpiperazin-1-yl)-N-(4-methylthiazol-2-yl)acetamide (21a): 4-methylthiazol-2-amine (1.0 g) was added to a round bottom flask, and then N, N-dimethylformamide (20 mL), 2-(4-methylpiperazin-1-yl)acetic acid (1.5 g), 2-(7-benzotriazole oxide)-N,N,N',N'-tetramethylurea hexafluorophosphate (5.0 g) and triethylamine (2.5 mL) were added. The reaction system was stirred for 14 hours under the gas argon protection at room temperature. After the reaction, the solvent in the system was dried by distillation under reduced pressure, and the resultant was diluted with water and extracted with ethyl acetate. The organic phase was washed with water and saturated saline solution respectively, and then dried with anhydrous sodium sulfate. The organic phase was filtered and dried by distillation under reduced pressure to obtain a crude product. The crude product was purified by pressurized silica gel column chromatography to obtain a pure product, MS (ESI) m/z (M+1)+: 255.13.

N-(4-methyl-5-(1-(tetrahydro-2H-pyran-2-yl)-1H-indazol-6-yl)thiazol-2-yl)-2-(4-methylpiperazin-1-yl)acetamide (21b): 2-(4-methylpiperazin-1-yl)-N-(4-methylthiazol-2-yl)acetamide (1.0 g) was added to a round bottom flask, and then dimethyl sulfoxide (10 mL)), 6-iodo-1-(tetrahydro-2H-pyran-2-yl)-1H-indazole (1.3 g), tetrakistriphenylphosphine palladium (0.45 g) and cesium carbonate (3.8 g) were added. The reaction system was heated to 130° C. and reacted for 14 hours under the gas argon protection. After the reaction, the solvent in the system was dried by distillation under reduced pressure, and the resultant was diluted with water and extracted with ethyl acetate. The organic phase was washed with water and saturated saline solution respectively, and then dried with anhydrous sodium sulfate. The organic phase was filtered and dried by distillation under reduced pressure to obtain a crude product. The crude product was purified by pressurized silica gel column chromatography to obtain a pure product, MS (ESI) m/z (M+1)+: 455.23.

N-(5-(1H-indazol-6-yl)-4-methylthiazol-2-yl)-2-(4-methylpiperazin-1-yl)acetamide (21c): N-(4-methyl-5-(1-(tetrahydro-2H-pyran-2-yl)-1H-indazol-6-yl)thiazol-2-yl)-2-(4-methylpiperazin-1-yl)acetamide (1.0 g), ethanol (10 mL), and 6 mol/liter hydrochloric acid (5 mL) were added to a 50 mL round bottom flask. The reaction system was heated to 90° C. and reacted for 14 hours under the gas argon protection. After the reaction, the solvent in the system was dried by distillation under reduced pressure, and the resultant was neutralized with saturated sodium bicarbonate to pH>10, a solid precipitated out and was filtered to obtain a crude product. The crude product was washed with ethyl acetate to obtain a pure product, MS (ESI) m/z (M+1)+: 371.17.

N-(5-(3-iodo-1H-indazole-6-yl)-4-methylthiazol-2-yl)-2-(4-methylpiperazin-1-yl)acetamide (21d): N-(5-(1H-indazol-6-yl)-4-methylthiazol-2-yl)-2-(4-methylpiperazin-1-yl)acetamide (0.6 g) was added to a 50 mL round bottom flask, and then N,N-dimethyl formamide (10 mL), iodine (0.8 g) and potassium hydroxide (0.4 g) were added. The reaction system was stirred for 8 hours under the gas argon protection at room temperature. After the reaction, the solvent in the system was dried by distillation under reduced pressure, and the resultant was diluted with water, the aqueous phase was extracted with ethyl acetate, the organic phase was washed with water and saturated saline solution respectively, and then dried with anhydrous sodium sulfate. The organic phase was filtered and dried by distillation under reduced pressure to obtain a crude product. The crude product was purified by pressurized silica gel column chromatography to obtain a pure product, MS (ESI) m/z (M+1)+: 497.06.

N-(5-(1-acetyl-3-iodo-1H-indazol-6-yl)-4-methylthiazol-2-yl)-2-(4-methylpiperazin-1-yl)acetamide (21e): N-(5-(3-iodo-1H-indazole-6-yl)-4-methylthiazol-2-yl)-2-(4-methylpiperazin-1-yl)acetamide (0.5 g) was added to a 50 mL round bottom flask, and then anhydrous dichloromethane (10 mL), triethylamine (0.3 mL), and acetyl chloride (0.1 g) were added. The reaction system was reacted for 4 hours under argon protection at room temperature. After the reaction, the solvent in the system was dried by distillation under reduced pressure, the resultant was neutralized with saturated sodium bicarbonate to pH>10, and then extracted with ethyl acetate. The organic phase was washed with water and saturated saline solution respectively, and then dried with anhydrous sodium sulfate. The organic phase was filtered and dried by distillation under reduced pressure to obtain a crude product. The crude product was purified by pressurized silica gel column chromatography to obtain a pure product, MS (ESI) m/z (M+1)+: 538.07.

N-(4-methyl-5-(3-(1-methyl-1H-pyrazol-4-yl)-1H-indazol-6-yl)thiazol-2-yl)-2-(4-methylpiperazin-1-yl)acetamide (21): N-(5-(1-acetyl-3-iodo-1H-indazol-6-yl)-4-methylthiazol-2-yl)-2-(4-methyl piperazin-1-yl)acetamide (0.1 g) was added to a round bottom flask, and then 1,4-dioxane (10 mL), water (2 mL), (1-methyl-1H-pyrazol-4-yl)boric acid (0.03 g)), tetrakistriphenylphosphine palladium (0.02 g) and potassium carbonate (0.07 g) were added. The reaction system was heated to 80° C. and reacted for 14 hours under the gas argon protection. After the reaction, the solvent in the system was dried by distillation under reduced pressure, and the resultant was diluted with water and then extracted with ethyl acetate. The organic phase was washed with water and saturated saline solution respectively, and then dried with anhydrous sodium sulfate. The organic phase was filtered and dried by distillation under reduced pressure to obtain a crude product. The crude product was purified by pressurized silica gel column chromatography to obtain Compound 21, MS (ESI) m/z (M+1)+: 451.21.

Example 22: (E)-2-hydroxyl-4-methyl-N-(4-methyl-5-(3-(2-(pyridin-2-yl)vinyl)-1H-indazol-6-yl)thiazol-2-yl)pentanamide

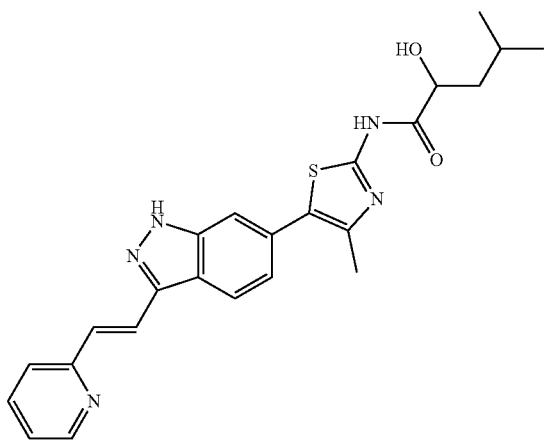 [SMILES: Cc1nc(NC(=O)C(O)CC(C)C)sc1-c1ccc2c(/C=C/c3ccccn3)n[nH]c2c1]

The synthesis of Example 22 was done using steps similar to those described in Example 1. MS (ESI) m/z (M+1)+: 448.18.

Example 23: N-(5-(3-(2-aminopyrimidin-5-yl)-1H-indazol-6-yl)-4-methylthiazol-2-yl)-2-(4-methylpiperazin-1-yl)acetamide

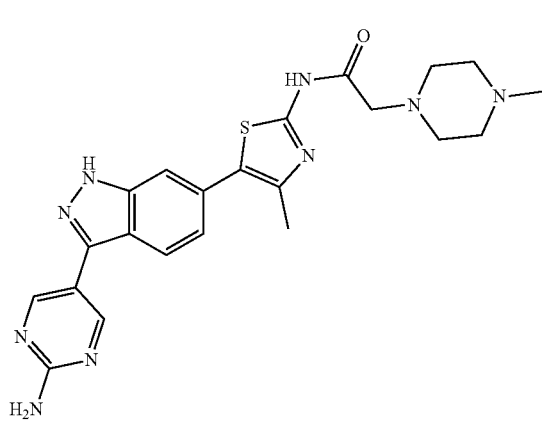 [SMILES: Cc1nc(NC(=O)CN2CCN(C)CC2)sc1-c1ccc2c(-c3cnc(N)nc3)n[nH]c2c1]

The synthesis of Example 23 was done using steps similar to those described in Example 21. MS (ESI) m/z (M+1)+: 464.20.

Example 24: N-(4-methyl-5-(3-(pyridin-3-yl)-1H-indazol-6-yl)thiazol-2-yl)-2-(4-methyl piperazin-1-yl)acetamide

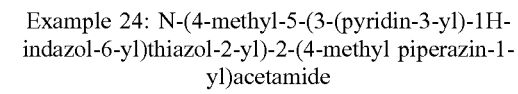

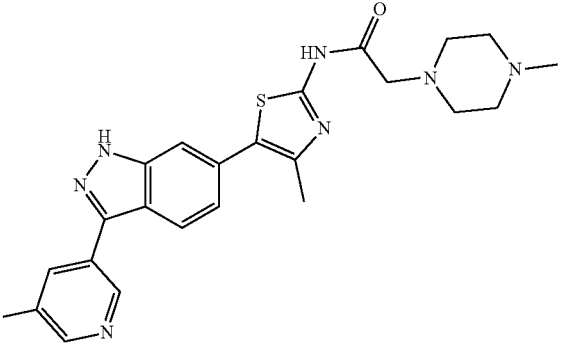

The synthesis of Example 24 was done using steps similar to those described in Example 21. MS (ESI) m/z (M+1)+: 448.19.

Example 25: N-(5-(3-(5-fluoropyridin-3-yl)-1H-indazol-6-yl)-4-methylthiazole-2-yl)-2-(4-methylpiperazin-1-yl)acetamide The synthesis of Example 25 was done using steps similar to those described in Example 21. MS (ESI) m/z (M+1)+: 466.18.

Example 26: N-(5-(3-(3-fluorophenyl)-1H-indazol-6-yl)-4-methylthiazol-2-yl)-2-(4-methylpiperazin-1-yl)acetamide Example 28: N-(4-methyl-5-(3-(pyridin-3-yl)-1H-indazol-6-yl)thiazol-2-yl)-2-(3-(trifluoromethyl)phenyl)acetamide

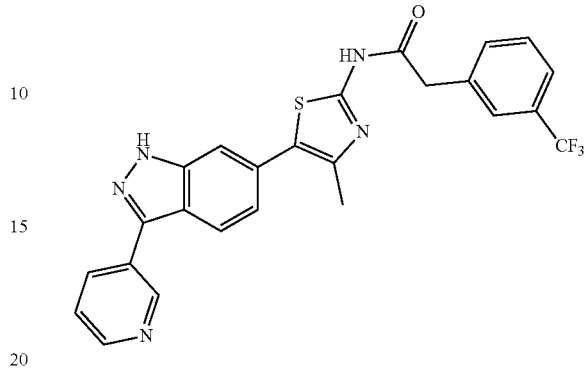

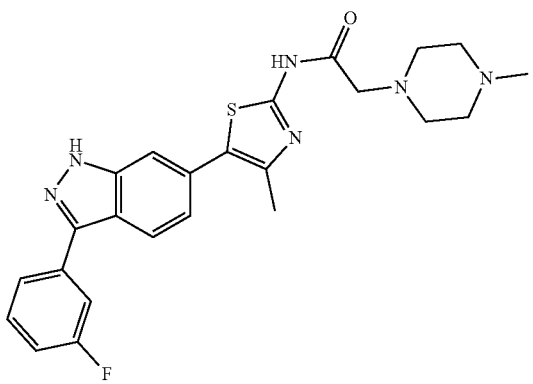 [SMILES: Cc1nc(NC(=O)CN2CCN(C)CC2)sc1-c1ccc2c(-c3cccc(F)c3)n[nH]c2c1]

The synthesis of Example 28 was done using steps similar to those described in Example 21. MS (ESI) m/z (M+1)+: 494.13.

Example 29: (E)-1-(4-methyl-5-(3-(2-(pyridin-2-yl)vinyl)-1H-indazol-6-yl)thiazol-2-yl)-3-(3-(trifluoromethyl)phenyl)urea

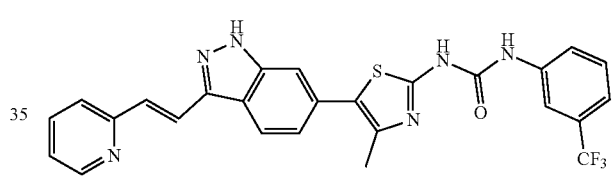

The synthesis of Example 26 was done using steps similar to those described in Example 21. MS (ESI) m/z (M+1)+: 465.19.

The synthesis of Example 29 was done using steps similar to those described in Example 1. MS (ESI) m/z (M+1)+: 521.14.

Example 27: (E)-N-(4-methyl-5-(3-(2-(pyridin-2-yl)vinyl)-1H-indazol-6-yl)thiazol-2-yl)-2-(1-methylpiperidin-4-yl)acetamide Example 30: (E)-N-(4-methyl-5-(3-(2-(pyridin-2-yl)vinyl)-1H-indazol-6-yl)thiazol-2-yl) acetamide

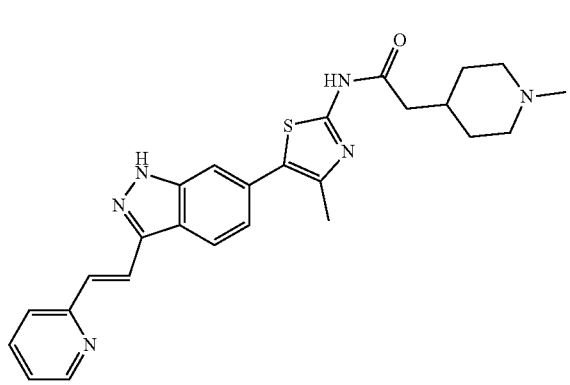 [SMILES: Cc1nc(NC(=O)CC2CCN(C)CC2)sc1-c1ccc2c(/C=C/c3ccccn3)n[nH]c2c1]

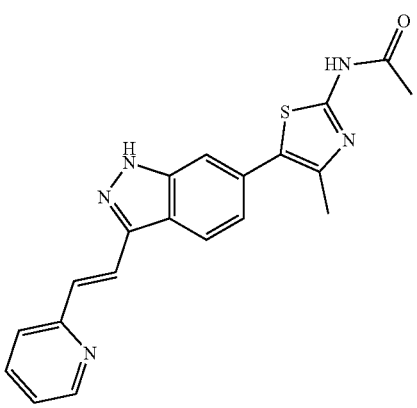 [SMILES: CC(=O)Nc1nc(C)c(-c2ccc3c(/C=C/c4ccccn4)n[nH]c3c2)s1]

The synthesis of Example 27 was done using steps similar to those described in Example 1. MS (ESI) m/z (M+1)+: 473.21.

The synthesis of Example 30 was done using steps similar to those described in Example 1. MS (ESI) m/z (M+1)+: 376.13.

Example 31: Effects on Cancer Cell Proliferation

By testing the effects of the Compound of the present invention on the growth of cancer cells (Table 2), the inhibitory effects of the compounds in the text on the proliferation of cancer cells and their selectivity in inhibiting the proliferation of cancer cells were further evaluated.

In this example, human gastrointestinal stromal tumor cell line GIST-T1 (expressing wild-type C-KIT gene) (purchased from Cosmo Bio Co., Ltd. (Japan)), human gastrointestinal stromal tumor cell line GIST-T1-T670I (expressing C-KIT-T670I mutant gene) (constructed by our laboratory with CRISPR technology), mouse primary B cell BaF3 (purchased from ATCC) were used. In addition, in this Example, mouse Tel-cKit-BaF3 (stably expressing C-KIT wild-type kinase), mouse Tel-cKit/T670I-BaF3 (stably expressing cKIT T670I mutant kinase), mouse Tel-PDGFRα-BaF3 (stably expressing PDGFRα kinase), mouse Tel-PDGFRβ-BaF3 (stably expressing PDGFRβ kinase), mouse Tel-VEGFR2-BaF3 (stably expressing VEGFR2 kinase), mouse Tel-FLT3-BaF3 (stably expressing FLT3 kinase) were also used. The above cell lines were all constructed by our laboratory. The construction method was as follows: the human C-KIT, C-KIT T670I, PDGFRα, PDGFRβ, VEGFR2, FLT3 kinase region sequences were amplified by PCR respectively and inserted into MSCV-Puro vector (purchased from Clontech) with N-terminal TEL fragment and/or NPM fragment and/or TPR fragment respectively, which was stably transferred into mouse BaF3 cells by retroviral method, and IL-3 growth factor was removed, and finally the cell lines in which protein was transferred depending on C-KIT, C-KIT/T670I, PDGFRα, PDGFRβ, VEGFR2, FLT3 were obtained. The GIST-T1-T670I (expressing C-KIT-T670I mutant gene) cell line was constructed by our laboratory. The construction method was as follows: the sgRNA targeting near the T670 site of the KIT gene was designed by the CRISPR design tool of the Zhang Feng Laboratory of the Massachusetts Institute of Technology (URL: crispr.mit.edu) and cloned into pSpCas9(BB)-2A-Puro vector (Addgene, USA); the obtained vector and a single-stranded oligonucleotide with T670I mutation near the T670 site were co-transfected into the cells, and after antibiotic selection, they were diluted and cultured in a single cell in a 96-well plate; the T670 site of the cells was sequenced and verified by the Sanger sequencing method.

In the Example, different concentrations (0.000508 µM, 0.00152 µM, 0.00457 µM, 0.0137 µM, 0.0411 µM, 0.123 µM, 0.370 µM, 1.11 µM, 3.33 µM, 10 µM in DMSO) of the Compound of the present invention and the control compound Axitinib (purchased from MedChem Express, China) was added to the above-mentioned cells, which were incubated for 72 hours, and the incubated cells were detected by the CCK-8 cell viability detection kit (purchased from Beibo Biological Company, Shanghai, China) (CCK-8 can be reduced to a highly water-soluble yellow formazan product by the dehydrogenase in the living cells, and the amount of formazan produced is proportional to the number of living cells), and the number of living cells was quantified by a microplate reader. And the GI50 of each compound and the control compound were calculated (the results were shown in Table 2 and Table 3).

The experimental results shown in Table 2 showed that the Compound of the present invention had a certain inhibitory effect on mutant cKIT-T670I, VEGFR2, PDGFRα, PDGFRβ, and FLT3, especially when compared with cKIT wild-type, it had stronger inhibitory effect on mutant cKIT-T670I. Compared with Axitinib, the preferred compound of the present invention had comparable or stronger inhibitory activity against mutant cKIT-T670I, but had relatively weak inhibitory activity against wild-type cKIT. cKIT wild-type played a very important role in the early development of normal hematopoietic stem cells. Therefore, in unnecessary cases, the inhibition of cKIT kinase would cause mechanistic toxicity, and it had been reported in the literature that simultaneous inhibition of FLT3 and cKIT would cause myelosuppressive toxicity. In addition, Axitinib had a certain inhibitory effect on the female parent BaF3 cells, and there was no selectivity between the wild-type cKIT and the mutant cKIT-T670I; the Compound of the present invention exhibited obvious selective inhibition among the mutant cKIT-T670I and the wild-type cKIT and the female parent BaF3 cells, which indicated that the preferred compound of the present invention inhibited the mutant cKIT-T670I without causing the problem of myelosuppressive toxicity due to the inhibition of wild-type cKIT and FLT3.

TABLE 2

| Compound | BaF3 | TEL-cKIT-BaF3 | TEL-cKIT/T670I-BaF3 | TEL-VEGFR2-BaF3 | TEL-PDGFRα-BaF3 | TEL-PDGFRβ-BaF3 | TEL-FLT3-BaF3 |
|---|---|---|---|---|---|---|---|
| 1 | 0.058 | 0.024 | 0.003 | 0.016 | 0.001 | 0.003 | <0.001 |
| 2 | >10 | 0.135 | 0.084 | 0.04 | 0.002 | 0.013 | 0.004 |
| 3 | 2.31 | 0.035 | 0.028 | 0.013 | 0.002 | 0.012 | 0.0001 |
| 4 | >10 | 1.55 | 0.006 | 0.007 | 0.002 | 0.001 | 0.004 |
| 5 | 2.92 | 0.425 | 0.009 | 0.038 | 0.002 | 0.011 | <0.001 |
| 6 | >10 | 0.024 | 0.012 | 0.005 | 0.001 | 0.003 | 0.002 |
| 7 | 3.69 | 0.191 | 0.094 | 0.015 | 0.0029 | | 0.003 |
| 8 | 4.87 | 0.216 | 0.019 | 0.019 | 0.0012 | | 0.0004 |
| 9 | 1.4 | 0.923 | 0.009 | 0.18 | <0.001 | | 0.001 |
| 10 | 4.1 | 0.07 | 0.037 | 0.0098 | 0.0013 | | 0.002 |
| 11 | 0.98 | 0.48 | 0.038 | 0.35 | 0.0013 | 0.0039 | 0.048 |
| 14 | 3.1 | 0.137 | 0.085 | 0.042 | 0.0074 | 0.018 | 0.0016 |
| 15 | 0.594 | 0.961 | 0.016 | | | | 0.002 |
| 16 | 1.51 | 1.35 | 0.323 | | | | 2.15 |
| 17 | 0.544 | 0.46 | 0.088 | | | | 0.004 |
| 18 | 0.706 | 0.507 | 0.037 | | | | 0.006 |
| 19 | 1.58 | 0.519 | 0.041 | | | | 0.004 |
| 20 | 0.708 | 0.361 | 0.037 | | | | 0.003 |
| 21 | >10 | 2.74 | 0.984 | | | | 0.068 |
| 22 | 1.53 | 1.01 | 0.034 | | | | 0.002 |
| 23 | 1.56 | 0.133 | 0.013 | | | | 0.0005 |

TABLE 2-continued

| Compound | BaF3 | TEL-cKIT-BaF3 | TEL-cKIT/T670I-BaF3 | TEL-VEGFR2-BaF3 | TEL-PDGFRα-BaF3 | TEL-PDGFRβ-BaF3 | TEL-FLT3-BaF3 |
|---|---|---|---|---|---|---|---|
| 24 | 5.13 | 3.21 | 0.114 | | | | 0.012 |
| 25 | 1.69 | 1.46 | 0.241 | | | | 0.018 |
| 26 | 1.04 | 1.02 | 0.083 | | | | 0.026 |
| 27 | 0.605 | 0.094 | 0.001 | | | | <0.001 |
| 28 | 2.49 | 0.048 | 0.007 | | | | 0.0001 |
| 29 | 0.105 | 0.025 | 0.038 | 0.004 | <0.001 | <0.001 | 0.002 |
| 30 | 1.46 | 0.047 | 0.008 | 0.012 | 0.001 | 0.001 | 0.0003 |
| Axitinib | 0.43 | 0.02 | 0.048 | <0.0001 | 0.0014 | 0.002 | 0.3 |

As shown in Table 3, the effects of Compound 7 and 9 of the present invention and the control compound Imatinib (purchased from MedChem Express, China) on gastrointestinal stromal tumor cell line GIST-T1 and the mutant GIST-T1-T670I cell line resistant to Imaitinib constructed by our laboratory were tested, and it was found that the Compound of the present invention not only had a strong inhibitory effect on Imatinib-sensitive gastrointestinal stromal tumors, but also had a strong inhibitory effect on Imatinib-resistant GIST-T1-T670I. This indicated that the Compound of the present invention can be used to treat gastrointestinal stromal tumors with T670I mutation.

TABLE 3

| $GI_{50}$ (μM) | GIST-T1 | GIST-T1-T670I |
|---|---|---|
| Imaitnib | 0.010 | >10 |
| 7 | 0.032 | 0.065 |
| 9 | 0.019 | 0.039 |

Example 32: Animal Experiment

In this example, the experimental results of Compound 9 in TEL-cKIT/T670I-BaF3 and GIST-T1-T670I mouse models were tested respectively.

The experimental steps were as follows:

(1) 4-6 weeks old Bal b/c female mice were purchased from Beijing Weitong Lihua Experimental Animal Co., Ltd. and were reared in SPF-level laboratories. Drinking water and litter were sterilized by autoclaving. All operations on mice were performed under sterile conditions.

(2) On day 0, about $5 \times 10^6$ TEL-cKIT/T670I-BaF3 or $5 \times 10^6$ GIST-T1-T670I cells were injected subcutaneously on the left back of all mice, respectively.

(3) For the mouse model of TEL-cKIT/T670I-BaF3, starting from day 6, the corresponding mice were orally administered every day methyl cellulose (HKI) vehicle (5 mice); Compound 9 at a dose of 10 mg/kg, 20 mg/kg, 40 mg/kg, 100 mg/kg mouse weight (5 mice each); sunitinib (purchased from MedChemExpress, China) at a dose of 40 mg/kg mouse weight (5 mice). For the mouse model of GIST-T1-T670I, starting from day 15, the corresponding mice were orally administered every day methyl cellulose (HKI) vehicle (5 mice); Compound 9 at a dose of 20 mg/kg, 30 mg/kg, 40 mg/kg (5 mice each); sunitinib at a dose of 40 mg/kg mouse weight (5 mice).

(4) Starting from day 6 (the mouse model of TEL-cKIT/T670I-BaF3) and day 15 (the mouse model of GIST-T1-T670I), the length/width of the subcutaneous tumors was measured with a vernier caliper every day, the body weight of the mice was recorded every day, and the effect of compound 9 on the body weight of the mice was determined respectively.

(5) The growth trend of subendothelial tumors was calculated, with the calculation method of tumor volume: length×width×width/2 $mm^3$.

Figure 1B:
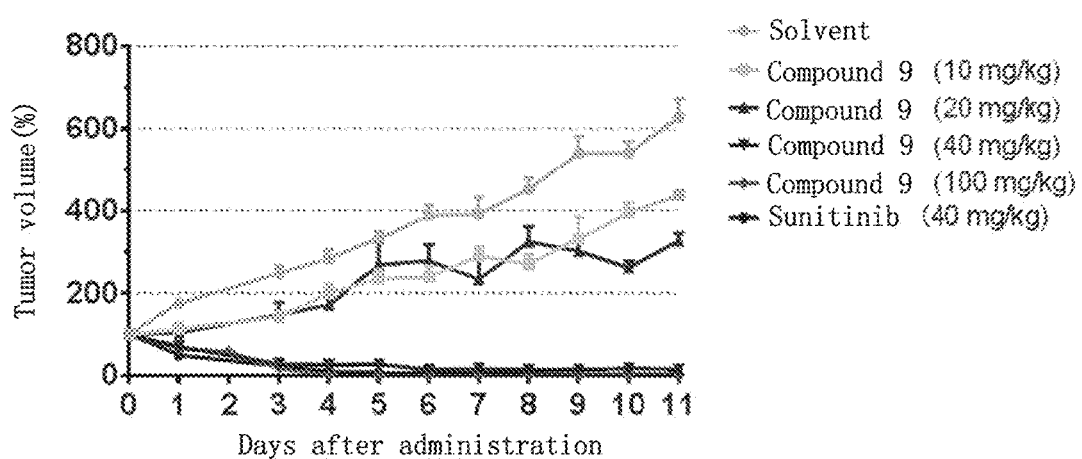
FIG. 1b shows the tumor suppression effects of Compound 9 and Sunitinib in the tel-cKIT/T670I-BaF3 cell tumor transplantation mouse models.
Figure 2A:
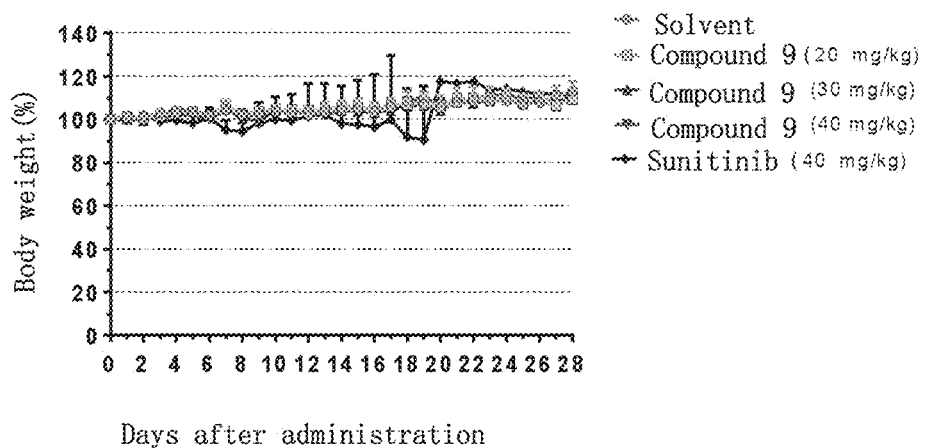
FIG. 2a shows the effects of Compound 9 and Sunitinib on the body weight of mice after administration in the GIST-T1-T670I cell tumor transplantation mouse models.
Figure 2B:
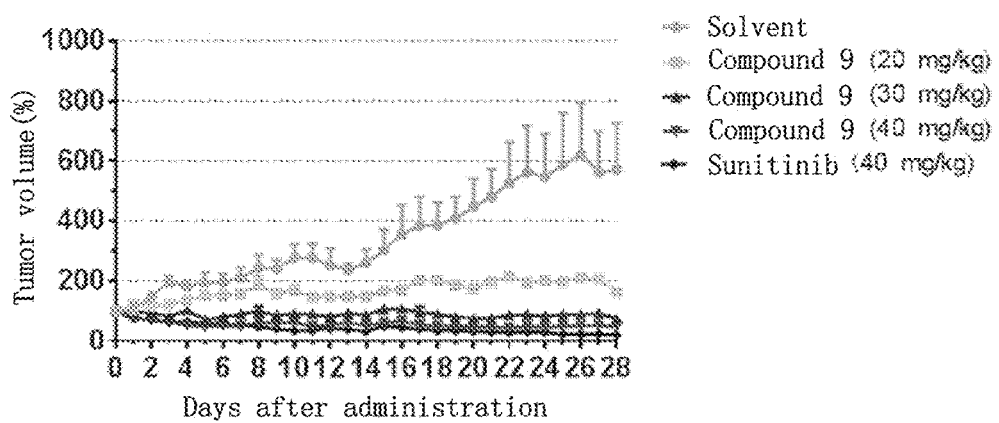
FIG. 2b shows the tumor suppression effects of Compound 9 and Sunitinib in the GIST-T1-T670I cell tumor transplantation mouse models.

The experimental results were shown in FIGS. 1a-b and 2a-b. Compound 9 had shown a certain inhibitory effect on mouse tumors in TEL-cKIT/T670I-BaF3 and GIST-T1-T670I mouse tumor models at a dose of 40 mg/kg, and with the increase of the number of days of treatment, the inhibitory effect of Compound 9 on mouse tumors was becoming more and more significant, and the tumor inhibition rate was as high as 80%. When 100 mg/kg Compound 9 was used, the tumor inhibition rate reached 100% on day 11 after administration in the TEL-cKIT/T670I-BaF3 mouse model. When 40 mg/kg Compound 9 was used, the tumor inhibition rate was 84.3% on day 28 after administration in the GIST-T1-T670I mouse model. Compound 9 not only effectively inhibited tumor growth in mice, but also had no effect on the body weight of mice, indicating that Compound 9 was suitable for animal administration. This also proved that the CKIT/T670I inhibitor compound of the present invention can be used to treat gastrointestinal stromal tumors with T670I mutation.

The present invention provides a novel kinase inhibitor compound, which can be used in reducing or inhibiting the kinase activity of cKIT (especially mutant cKIT/T670I), FLT3 (including mutant FLT3-ITD), PDGFRα, PDGFRβ, and/or VEGFR2 in cells or subjects, and/or preventing or treating a disorder related to the activity of cKIT (especially mutant cKIT/T670I), FLT3 (including mutant FLT3-ITD), PDGFRα, PDGFRβ, and/or VEGFR2 in subjects. Therefore, it can be prepared as corresponding medicament and has industrial applicability.

INDUSTRIAL APPLICABILITY

The present invention provides a novel kinase inhibitor compound, which can be used in reducing or inhibiting the kinase activity of cKIT (especially mutant cKIT/T670I), FLT3 (including mutant FLT3-ITD), PDGFRα, PDGFRβ, and/or VEGFR2 in cells or subjects, and/or preventing or treating a disorder related to the activity of cKIT (especially mutant cKIT/T670I), FLT3 (including mutant FLT3-ITD), PDGFRα, PDGFRβ, and/or VEGFR2 in subjects. Therefore, it can be prepared as corresponding medicament and has industrial applicability.

While the invention has been described in detail herein, the invention is not limited thereto and modifications may be made by those skilled in the art based on the principles of the invention, and thus, all modifications in accordance with the principles of the invention are to be understood as within the protection scope of the invention.

The invention claimed is:
1. A kinase inhibitor, comprising a compound of formula (I), or a pharmaceutically acceptable salt, solvate, ester, acid, or prodrug thereof,

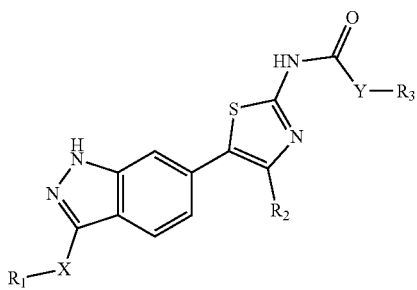

Formula (I)

wherein,
X is —(CH=CH);
Y is selected from the group consisting of —NH— and —(CH$_2$)$_n$—, where n is an integer of 0 to 3;
R$_1$ is selected from the group consisting of phenyl optionally substituted with 1-3 independent R$_4$ groups, pyridinyl optionally substituted with 1-3 independent R$_4$ groups, pyrazolyl optionally substituted with 1-3 independent R$_4$ groups, and pyrimidinyl optionally substituted with 1-3 independent R$_4$ groups;
R$_2$ is selected from the group consisting of hydrogen and C$_{1-6}$ alkyl;
R$_3$ is selected from the group consisting of C$_{1-6}$ alkyl optionally substituted with 1-2 independent R$_5$ groups, C$_{1-6}$ alkylamino, as well as phenyl optionally substituted with 1-3 independent R$_4$ groups, naphthyl optionally substituted with 1-3 independent R$_4$ groups, pyridinyl optionally substituted with 1-3 independent R$_4$ groups, piperazinyl optionally substituted with 1-3 independent R$_4$ groups, and piperidyl optionally substituted with 1-3 independent R$_4$ groups;
R$_4$ is independently selected from the group consisting of halogen, amino, C$_{1-6}$ alkyl, C$_{3-6}$ cycloalkyl, C$_{1-6}$ haloalkyl, C$_{1-6}$ alkoxy, C$_{1-6}$ hydroxyalkyl, C$_{1-6}$ alkylamino, C$_{2-6}$ alkylamide, (4-methylpiperazin-1-yl) methyl, morpholinomethyl, morpholinyl, 4-methylpiperazin-1-yl, 4-piperidyl, and 4-tetrahydropyranyl;
R$_5$ is independently selected from the group consisting of amino, hydroxyl, and C$_{1-6}$ alkylthio.

2. The kinase inhibitor according to claim 1, wherein Y is a direct bond or —CH$_2$—.

3. The kinase inhibitor according to claim 1, wherein R$_1$ is selected from the group consisting of phenyl, pyridinyl, pyrazolyl, and pyrimidinyl groups optionally substituted with 1-3 independent R$_4$ groups, wherein R$_4$ is independently selected from the group consisting of halogen, amino, C$_{1-6}$ alkyl, C$_{1-6}$ haloalkyl, C$_{1-6}$ alkoxy, and (4-methylpiperazin-1-yl)methyl.

4. The kinase inhibitor according to claim 3, wherein R$_1$ is selected from the group consisting of phenyl, 2-pyridinyl, 3-pyridinyl, 4-pyrazolyl, and 5-pyrimidinyl groups optionally substituted with methyl, amino or halogen.

5. The kinase inhibitor according to claim 1, wherein R$_2$ is hydrogen or methyl.

6. The kinase inhibitor according to claim 1, wherein R$_3$ is selected from the group consisting of C$_{1-6}$ alkyl optionally substituted with 1-2 independent R$_5$ groups, C$_{1-6}$ alkylamino, as well as phenyl, naphthyl, pyridinyl, piperazinyl and piperidyl groups optionally substituted with 1-3 independent R$_4$ groups, wherein R$_4$ is independently selected from the group consisting of halogen, amino, C$_{1-6}$ alkyl, C$_{1-6}$ haloalkyl, C$_{1-6}$ alkoxy, and (4-methylpiperazin-1-yl)methyl, R$_5$ is independently selected from the group consisting of amino, hydroxyl, and methylthio.

7. The kinase inhibitor according to claim 6, wherein R$_3$ is selected from the group consisting of C$_{1-6}$ alkyl optionally substituted with amino, hydroxy or methylthio; dimethylamino; N-piperazinyl optionally substituted with methyl; phenyl optionally substituted with halogen, trifluoromethyl or methoxy; naphthyl; 4-pyridinyl; 3-piperidyl; and 4-piperidyl optionally substituted with methyl.

8. The kinase inhibitor according to claim 1, wherein when Y is a direct bond, R$_3$ is selected from the group consisting of C$_{1-6}$ alkyl optionally substituted with amino, hydroxy or methylthio, and 4-pyridinyl; when Y is —CH$_2$—, R$_3$ is selected from the group consisting of phenyl optionally substituted with methoxy, N-piperazinyl optionally substituted with methyl, and 4-piperidyl optionally substituted with methyl.

9. The kinase inhibitor according to claim 1, wherein the compound is selected from the group consisting of:

| No. | Compound structure |
|---|---|
| 1 | 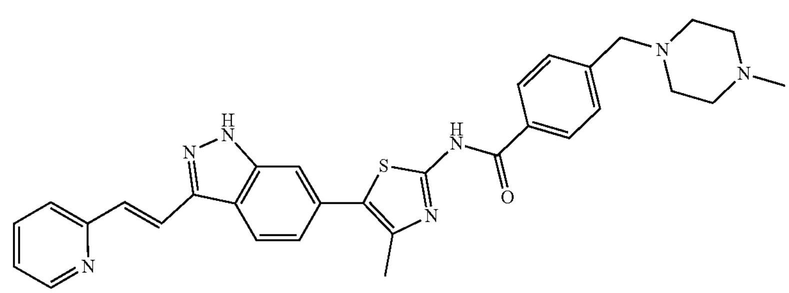 [SMILES: Cc1nc(NC(=O)c2ccc(CN3CCN(C)CC3)cc2)sc1-c1ccc2c(/C=C/c3ccccn3)n[nH]c2c1] |

-continued

| No. | Compound structure |
|---|---|
| 2 | 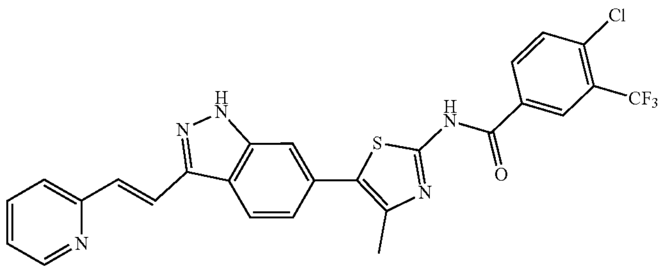 [SMILES: Cc1nc(NC(=O)c2ccc(Cl)c(C(F)(F)F)c2)sc1-c1ccc2c(/C=C/c3ccccn3)n[nH]c2c1] |
| 3 | 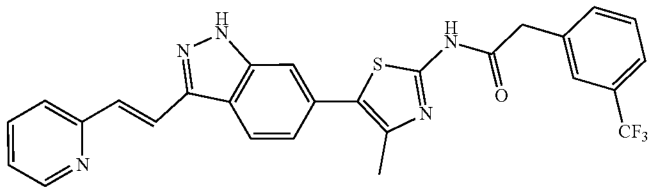 [SMILES: Cc1nc(NC(=O)Cc2cccc(C(F)(F)F)c2)sc1-c1ccc2c(/C=C/c3ccccn3)n[nH]c2c1] |
| 4 | 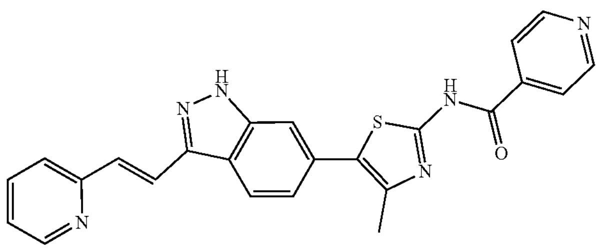 [SMILES: Cc1nc(NC(=O)c2ccncc2)sc1-c1ccc2c(/C=C/c3ccccn3)n[nH]c2c1] |
| 5 | 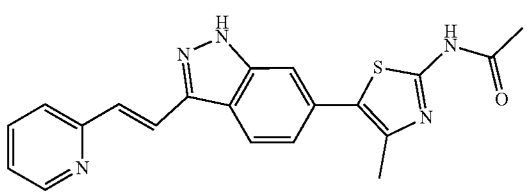 [SMILES: CC(=O)Nc1nc(C)c(-c2ccc3c(/C=C/c4ccccn4)n[nH]c3c2)s1] |
| 6 | 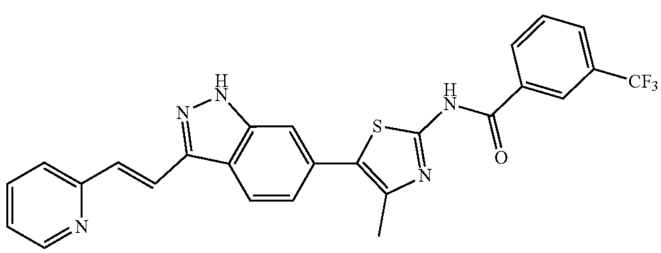 [SMILES: Cc1nc(NC(=O)c2cccc(C(F)(F)F)c2)sc1-c1ccc2c(/C=C/c3ccccn3)n[nH]c2c1] |
| 7 | 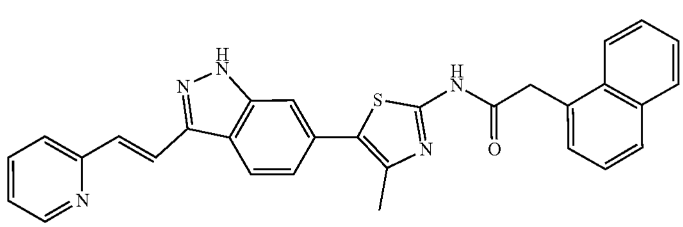 [SMILES: Cc1nc(NC(=O)Cc2cccc3ccccc23)sc1-c1ccc2c(/C=C/c3ccccn3)n[nH]c2c1] |
| 8 | 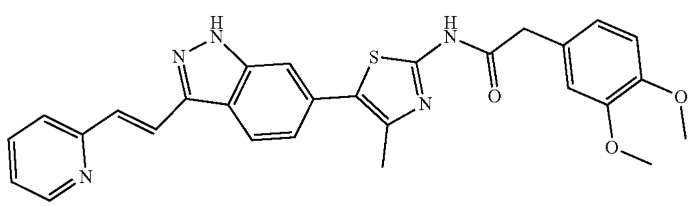 [SMILES: COc1ccc(CC(=O)Nc2nc(C)c(-c3ccc4c(/C=C/c5ccccn5)n[nH]c4c3)s2)cc1OC] |

| No. | Compound structure |
|---|---|
| 9 | 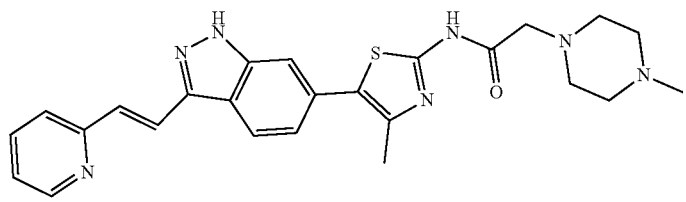 [SMILES: Cc1nc(NC(=O)CN2CCN(C)CC2)sc1-c1ccc2c(/C=C/c3ccccn3)n[nH]c2c1] |
| 10 | 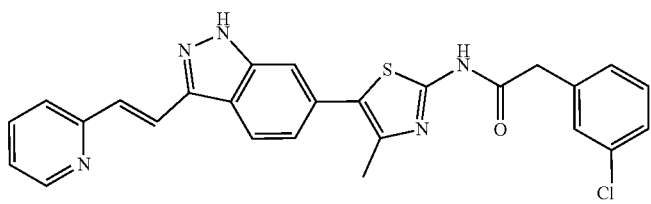 [SMILES: Cc1nc(NC(=O)Cc2cccc(Cl)c2)sc1-c1ccc2c(/C=C/c3ccccn3)n[nH]c2c1] |
| 11 | 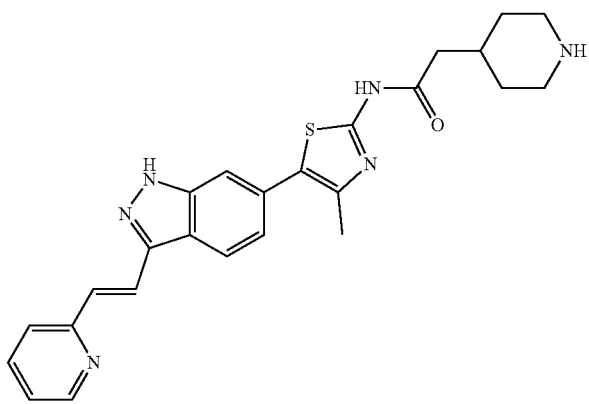 [SMILES: Cc1nc(NC(=O)CC2CCNCC2)sc1-c1ccc2c(/C=C/c3ccccn3)n[nH]c2c1] |
| 12 | 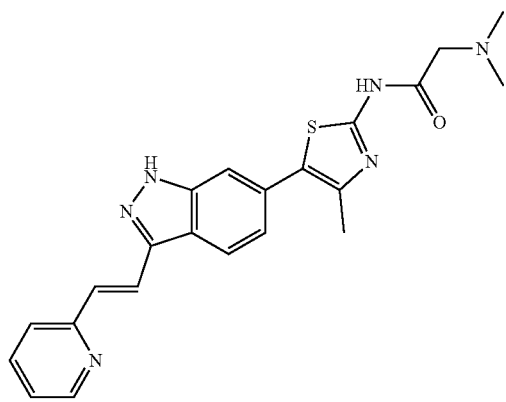 [SMILES: Cc1nc(NC(=O)CN(C)C)sc1-c1ccc2c(/C=C/c3ccccn3)n[nH]c2c1] |

| No. | Compound structure |
|---|---|
| 13 | 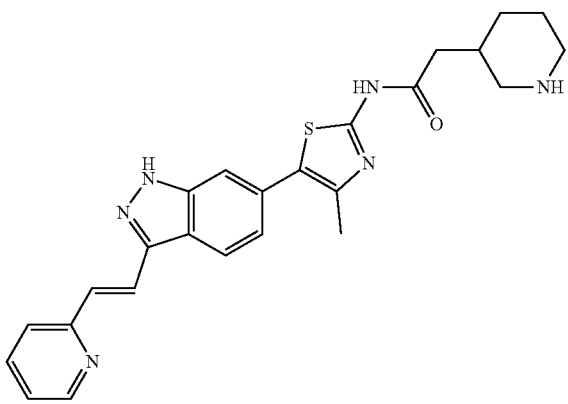 [SMILES: Cc1nc(NC(=O)CC2CCCNC2)sc1-c1ccc2c(/C=C/c3ccccn3)n[nH]c2c1] |
| 14 | 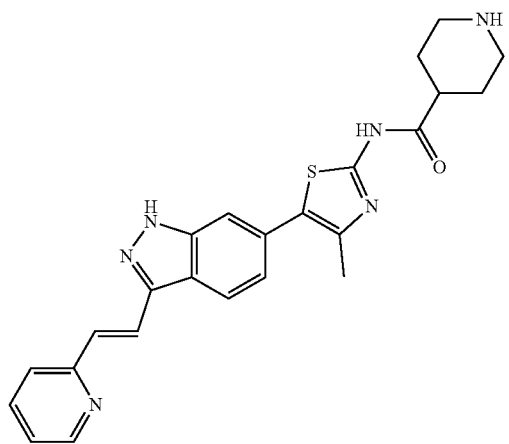 [SMILES: Cc1nc(NC(=O)C2CCNCC2)sc1-c1ccc2c(/C=C/c3ccccn3)n[nH]c2c1] |
| 15 | 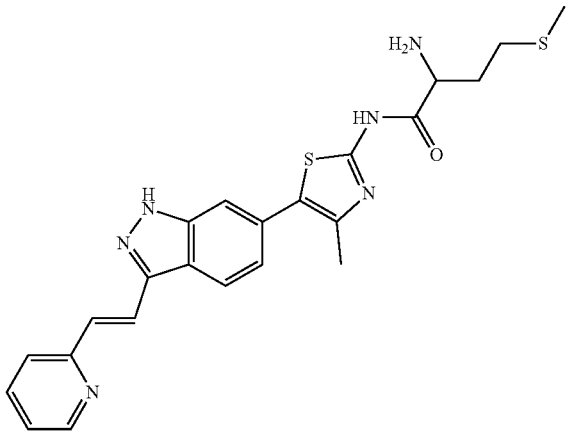 [SMILES: CSCCC(N)C(=O)Nc1nc(C)c(-c2ccc3c(/C=C/c4ccccn4)n[nH]c3c2)s1] |

-continued
| No. | Compound structure |
|---|---|
| 16 | 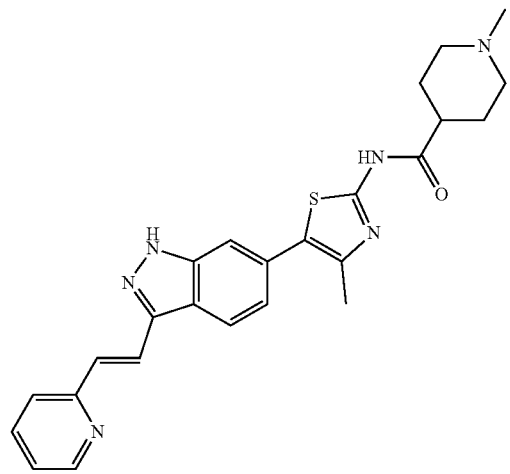 [SMILES: Cc1nc(NC(=O)C2CCN(C)CC2)sc1-c1ccc2c(/C=C/c3ccccn3)n[nH]c2c1] |
| 17 | 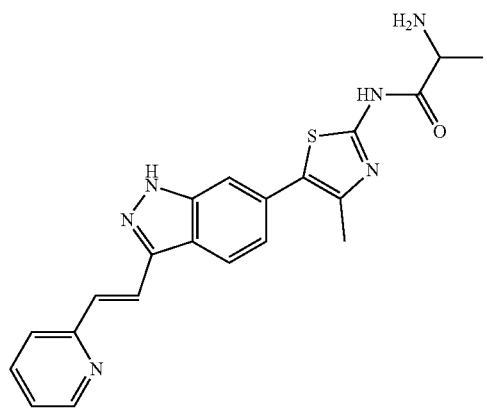 [SMILES: Cc1nc(NC(=O)C(C)N)sc1-c1ccc2c(/C=C/c3ccccn3)n[nH]c2c1] |
| 18 | 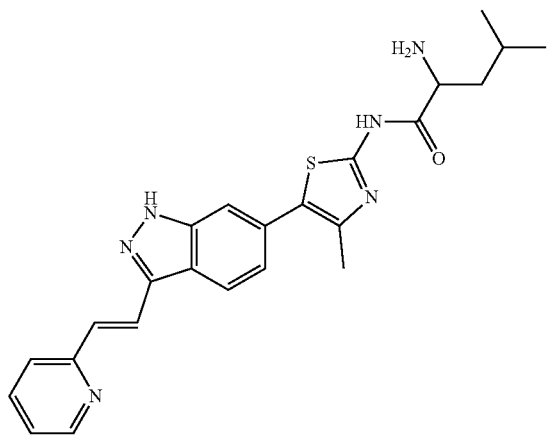 [SMILES: Cc1nc(NC(=O)C(N)CC(C)C)sc1-c1ccc2c(/C=C/c3ccccn3)n[nH]c2c1] |

-continued
| No. | Compound structure |
|---|---|
| 19 | 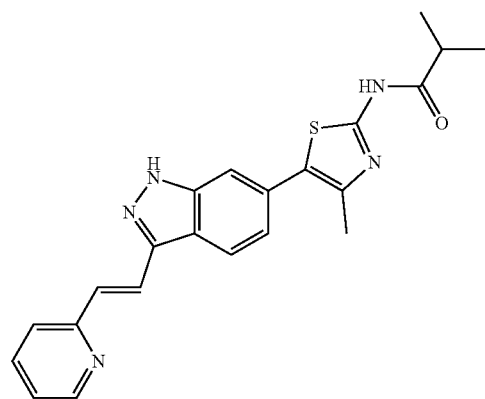 [SMILES: Cc1nc(NC(=O)C(C)C)sc1-c1ccc2c(/C=C/c3ccccn3)n[nH]c2c1] |
| 20 | 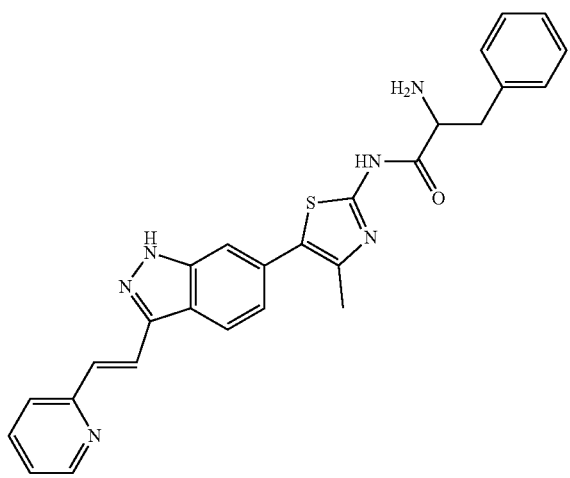 [SMILES: Cc1nc(NC(=O)C(N)Cc2ccccc2)sc1-c1ccc2c(/C=C/c3ccccn3)n[nH]c2c1] |
| 22 | 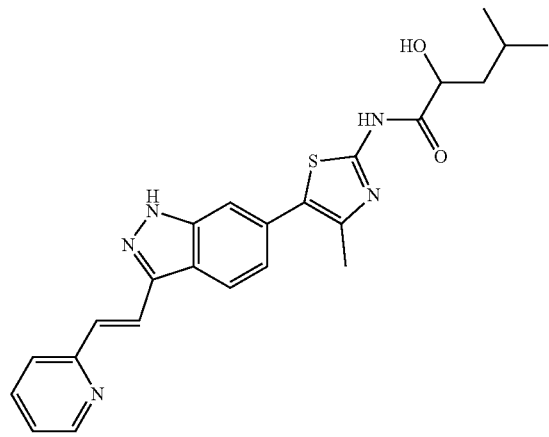 [SMILES: Cc1nc(NC(=O)C(O)CC(C)C)sc1-c1ccc2c(/C=C/c3ccccn3)n[nH]c2c1] |

| No. | Compound structure |
|---|---|
| 27 | 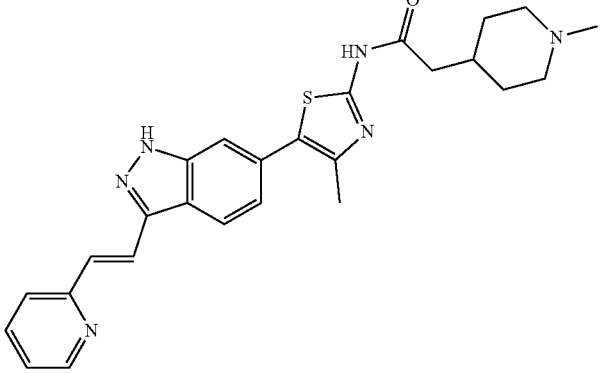 |
| 29 | 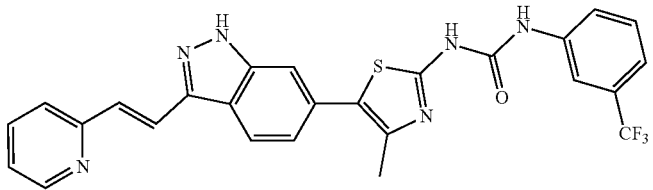 [SMILES: Cc1nc(NC(=O)Nc2cccc(C(F)(F)F)c2)sc1-c1ccc2c(/C=C/c3ccccn3)n[nH]c2c1] |
| 30 | 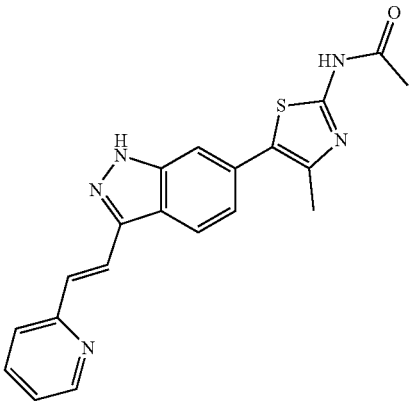 |

10. A pharmaceutical composition, comprising the kinase inhibitor according to claim 1, and a pharmaceutically acceptable carrier or excipient.

11. A method for treating or preventing a disease, disorder or condition related to the activity of cKIT, FLT3, PDGFRα, PDGFRβ, and/or VEGFR2, comprising administering the kinase inhibitor according to claim 1 to a subject having the disease, disorder or condition.

12. The method according to claim 11, wherein the disease, disorder or condition is cKIT-T670I mutant gastrointestinal stromal tumor.

13. The method according to claim 11, wherein the disease, disorder or condition is related to the activity of mutant cKIT-T670I.

* * * * *